(12) United States Patent
Palin et al.

(10) Patent No.: US 7,482,469 B2
(45) Date of Patent: Jan. 27, 2009

(54) 2-(BENZIMIDAZOL-1-YL)-ACETAMIDE BISARYL DERIVATIVES

(75) Inventors: Ronald Palin, Newhouse (GB); Colin Alasdair Gray, Newhouse (GB)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 11/593,741

(22) Filed: Nov. 7, 2006

(65) Prior Publication Data

US 2007/0112034 A1 May 17, 2007

Related U.S. Application Data

(60) Provisional application No. 60/734,457, filed on Nov. 8, 2005.

(51) Int. Cl.
*A61K 31/4184* (2006.01)
*C07D 235/08* (2006.01)

(52) U.S. Cl. .................................. 548/309.7; 514/394
(58) Field of Classification Search ............... 548/309.7
See application file for complete search history.

(56) References Cited

U.S. PATENT DOCUMENTS

2003/0078252 A1   4/2003   Sanner et al.

FOREIGN PATENT DOCUMENTS

| WO | WO 2004/100865 A2 | 11/2004 |
|----|-------------------|---------|
| WO | WO 2004/100865 A3 | 11/2004 |
| WO | WO 2006/033620 A1 | 3/2006  |

OTHER PUBLICATIONS

CA Registry No. 332018-23-2, indexed in the Registry file on STN on Apr. 23, 2001.*
CA Registry No. 6122-10-7, indexed in the Registry file on STN on Nov. 16, 1984.*
Mezey, E. et al., "Distribution of mRNA for vanilloid receptor subtype 1 (VR1), and VR1-like immunoreactivity, in the central nervous system of the rat and human," Proc. Natl. Acad. Sci., vol. 97, No. 7 (2000) pp. 3655-3660.
Caterina, M. J. et al., "The capsaicin receptor: a heat-activated ion channel in the pain pathway," Nature, vol. 389 (1997), pp. 816-824.
DiMarzo, V. et al., "Endovanilloid signaling pain," Current Opinion in Neurobiology, vol. 12 (2002) pp. 372-379.
Caterina, M. J. et al., "Impaired Nociception and Pain Sensation in Mice Lacking the Capsaicin Receptor," Science, vol. 288 (2000), pp. 306-313.
Davis, J. B. et al., "Vanilloid receptor-1 is essential for inflammatory thermal hyperalgesia," Nature, vol. 405 (2000) pp. 183-187.
Amaya, F. et al., "Local inflammation increases vanilloid receptor 1 expression within distinct subgroups of DRG neurons," Brain Research, vol. 963 (2003) pp. 190-196.
Rashid, H. et al., "Novel Expression of Vanilloid Receptor 1 on Capsaicin-Insensitive Fibers Accounts for the Analgesic Effect of Capsaicin Cream in Neuropathic Pain," The Journal of Pharmacology and Experimental Therapeutics, vol. 304 (2003) pp. 940-948.

Hong, S. et al., "Early Painful Diabetic Neuropathy Is Associated with Differential Changes in the Expression and Function of Vanilloid Receptor 1," The Journal of Biological Chemistry, vol. 280, No. 1 (2005) pp. 618-627.
Bley, K. R., "Recent developments in transient receptor potential vanilloid receptor 1 agonist-based therapies," Expert Opinion Investig. Drugs, vol. 13 (2004) pp. 1445-1456.
Walker, K. M. et al., "The VR1 Antagonist Capsazepine Reverses Mechanical Hyperalgesia in Models of Inflammatory and Neuropathic Pain," The Journal of Pharmacology and Experimental Therapeutics, vol. 304, No. 1 (2003) pp. 56-62.
Pomonis, J. D. et al., "N-(4-Tertiarybutylphenyl)-4-(3-cholorphyridin-2-yl)tetrahydrophyrazine-1(2H)-carbox-amide (BCTC), a Novel, Orally Effective Vanilloid Receptor 1 Antagonist with Analgesic Properties: II. In Vivo Characterization in Rat Models of Inflammatory and Neuropathic Pain," The Journal of Pharmacology and Experimental Therapeutics, vol. 306 (2003) pp. 387-393.
Birder, L. A. et al., "Altered urinary bladder function in mice lacking the vanilloid receptor TRPV1," Nature Neuroscience, vol. 5, No. 9 (2002) pp. 856-860.
Sharma, S. C., "Synthesis of New Local Anaesthetics: Part VIII—Synthesis of 4,5-Substituted Thiazoles," Indian J. Chem., vol. 4 (1966) pp. 33-36.
Das, J. et al., "Effects of positional and geometrical isomerism on the biological activity of some novel oxazolidinones," Bioorganic & Medicinal Chemistry Letters, vol. 15 (2005) pp. 337-343.

(Continued)

*Primary Examiner*—Laura L. Stockton
(74) *Attorney, Agent, or Firm*—Susan Hess

(57) ABSTRACT

The invention relates to 2-(benzimidazol-1-yl)-acetamide bisaryl derivative having the general Formula I

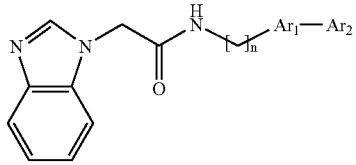

Formula I wherein n is 0 or 1; $Ar_1$ represents a diradical derived from a 5- or 6-membered aromatic ring, optionally comprising 1-3 heteroatoms selected from N, O and S, said ring being optionally substituted with $(C_{1-4})$alkyl, $(C_{1-4})$alkyloxy, halogen, $CF_3$ or cyano; $Ar_2$ represents a 6-membered aryl ring, optionally comprising 1-3 nitrogen atoms, said ring being optionally substituted with 1-3 substituents selected from $(C_{1-4})$alkyl (optionally substituted with 1 or more halogens), $(C_{1-4})$alkyloxy (optionally substituted with 1 or more halogens), di$(C_{1-4})$alkylamino, halogen, $CF_3$ or cyano; or a pharmaceutically acceptable salt thereof; to pharmaceutical compositions comprising the same and to the use of said 2-(benzimidazol-1-yl)-acetamide bisaryl derivatives in the treatment of TRPV1 mediated disorders.

18 Claims, No Drawings

OTHER PUBLICATIONS

Larsen, N. G. et al., "Bis-Benzimidazole-Appended Binucleating Porphyrin Ligands: Synthesis, Characterization, and X-ray Structure," J. Am. Chem. Soc., vol. 108 (1986) pp. 6950-6960.

Lin, N-H., et al., "Synthesis and Structure-Activity Relationships of 5-Substituted Pyridine Analogues of 3-[2-((S)-Pyrolidinyl)methoxy]pyridine, A-84543: A Potent Nicotinic Receptor Ligand," Bioorganic & Medicinal Chemistry Letters, vol. 11 (2001) pp. 631-633.

Breinholt, J. et al., "Syntheisis of 2-Amino-4$H$-thiazolo[5,4-$b$]indole and Characterization of its Colored Conversion Products with Protein Tyrosine Phosphatase Inhibitory Activity," J. Heterocyclic Chem., vol. 38 (2001) pp. 569-577.

Jagerovic, N. et al., "Long-Acting Fentanyl Analogues: Synthesis and Pharmacology of $N$-(1-Phenylpyrazolyl)-$N$-(1-phenylalkyl-4-piperidyl)propanamides," Bioorganic & Medicinal Chemistry, vol. 10 (2002) pp. 817-827.

Shtacher, G. et al., "Synthesis of Chelating Compounds to Be Used as Potential Bone Seekers," J. Med. Chem., vol. 9, No. 2 (1996) pp. 197-203.

Dubuisson, D. et al., "The Formalin Test: A Quantitative Study of the Analgesic Effects of Morphine, Meperidine, and Brain Stem Stimulation in Rats and Cats," Elsevier/North-Holland Biomedical Press, Pain, vol. 4 (1977) pp. 161-174.

Hirota et al., "The Effects of Local and Intravenous Anesthetics on Recombinant Rat VR1 Vanilloid Receptors", *Anesth Analog* 96:1656-1660 (2003).

Written Opinion dated May 14, 2008, International Application No. PCT/EP2006/068109.

Written Opinion dated May 14, 2008, International Application No. PCT/EP2006/068125.

\* cited by examiner

2-(BENZIMIDAZOL-1-YL)-ACETAMIDE BISARYL DERIVATIVES

The present invention relates to 2-(benzimidazol-1-yl)-acetamide derivatives, to pharmaceutical compositions comprising the same and to the use of these 2-(benzimidazol-1-yl)-acetamide derivatives in the treatment of TRPV1 related disorders.

The vanilloid receptor (VR1 or TRPV1), a non-selective ligand-gated cation channel belonging to the Transient Receptor Channel family (TRP family) of cation channels, is highly expressed on the peripheral termini of small diameter sensory neurones innervating many tissues including skin, bladder, airway and gastrointestinal tract. More specifically TRPV1 receptors are located on a subset Aδ and C fibres, the afferents commonly associated with nociception (Mezey et al., Proc. Natl. Acad. Sci. 97, 3655-3660, 2000). Characterisation of this channel at the molecular level identified it as the target of the vanilloid capsaicin, the main pungent constituent of hot chilli peppers (Caterina et al., Nature 389, 816-824, 1997). Indeed, sensitivity to capsaicin has been used for many years as a marker of nociceptor activity. These, polymodal nociceptors are activated by multiple noxious stimuli including chemical, mechanical and thermal. Study of the functional properties of TRPV1 demonstrated that this receptor shares many properties common to nociceptors including activation by thermal stimuli (>43° C.) and chemicals (including capsaicin and endovanilloids such as N-arachidonoyl-dopamine (NADA) and lipoxygenase metabolites), as well as sensitisation and activation by acidification. Furthermore, inflammatory mediators (including ATP and bradykinin) have been shown to functionally sensitise TRPV1 in vitro. This evidence suggests that TRPV1 has an integral role in the polymodal detection of noxious stimuli and contributes to the transduction of inflammatory pain responses and potentially also peripheral tissue injury (reviewed in Di Marzo et al., Curr. Opin. Neurobiol. 12, 372-379, 2002).

A role for TRPV1 in the detection of painful stimuli is also inferred from data in gene knockout mice. Mice null for TRPV1 show attenuated development of behavioural thermal hyperalgesia after an inflammatory insult (Caterina et al., Science 288, 306-313, 2000, Davis et al., Nature 405, 183-187, 2000). Small diameter sensory neurones from these animals also show altered responses to thermal and acid stimuli. Moreover, altered expression and/or functional activity of TRPV1 has been demonstrated following inflammation and nerve injury in animals models (Amaya et al., Brian Res. 963, 190-196, 2003, Rashid et al., J. Pharm. Exp. Ther. 304, 940-948, 2003, Hong & Wiley, J. Biol. Chem. 280, 618-627, 2005).

In humans, intradermal exposure to capsaicin leads at first to the sensation of burning pain due to neuronal excitation, followed by a long lasting period of analgesia which is believed to be a consequence of functional desensitisation (reviewed in Bley, Exp. Opin Investig Drugs. 13, 1445-1456, 2004). This led to the development of TRPV1 agonists as potential analgesic compounds. However, these compounds suffer from a number of issues including pain and a burning sensation on initial application. More recently, TRPV1 antagonists including capsazepine (Walker et al., J. Pharm. Exp. Ther. 304, 56-62, 2003) and BCTC (Pomonis et al., J. Phar. Exp. Ther. 306, 387-393, 2004) have been shown to be active in a variety of preclinical animal models of inflammatory and neuropathic pain.

In addition to a role in pain transduction there is also growing evidence for a role for TRPV1 in regulating afferent and efferent function of sensory nerves and the function of non-neuronal cells. Indeed, altered bladder function, with a higher frequency of low amplitude, non-voiding bladder contractions and an increase in bladder capacity has been observed by in TRPV1 KO mice (Birder et al., Nat. Neurosci. 5, 856-860, 2002). This may involve neuronal TRPV1 and TRPV1 expressed on uroepithelial cells. Thus, there is clear evidence to suggest that agents modulating TRPV1 activity will have utility not only in pain states and other diseases involving inflammation but also in conditions involving hyperactivity of primary sensory fibres (e.g. bladder overactivity and urge incontinence).

2-(Benzimidazol-1-yl)acetamide derivatives have been disclosed in the International Patent Applications WO 2004/100865 and WO 2006/033620 (AstraZeneca AB) as inhibitors of the TRPV1 receptor and useful in the treatment of TRPV1 mediated disorders, such as in the treatment of acute and chronic pain disorders, acute and chronic neuropathic pain, acute and chronic inflammatory pain, and respiratory diseases. There remains a need for additional compounds that are useful in the treatment of TRPV1 mediated disorders.

To this aim the present invention provides 2-(benzimidazol-1-yl)-acetamide bisaryl derivative having the general Formula I

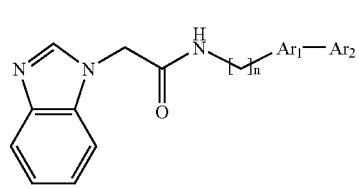

Formula I wherein n is 0 or 1;

$Ar_1$ represents a diradical derived from a 5- or 6-membered aromatic ring, optionally comprising 1-3 heteroatoms selected from N, O and S, said ring being optionally substituted with ($C_{1-4}$)alkyl, ($C_{1-4}$)alkyloxy, halogen, $CF_3$ or cyano;

$Ar_2$ represents a 6-membered aryl ring, optionally comprising 1-3 nitrogen atoms, said ring being optionally substituted with 1-3 substituents selected from ($C_{1-4}$)alkyl (optionally substituted with 1 or more halogens), ($C_{1-4}$)alkyloxy (optionally substituted with 1 or more halogens), di($C_{1-4}$) alkylamino, halogen, $CF_3$ or cyano; or a pharmaceutically acceptable salt thereof; with the proviso that derivatives wherein n is 0 and —$Ar_1$—$Ar_2$ represents 4-phenylthiazol-2-yl are excluded.

The excluded compounds relate to the disclosure thereof by S. C. Sharma (Indian J. Chem 4, 33-36, 1966) as local anaesthetics.

The 2-(benzimidazol-1-yl)-acetamide bisaryl derivatives of the present invention differ from the known 2-(benzimidazol-1-yl)-acetamide TRPV1 (vanilloid receptor) inhibitors described by AstraZeneca in WO 2004/100865 and in WO 2006/033620, in the presence of a biaryl (—$Ar_1$—$Ar_2$) group, combined with a benzimidazole moiety which is non-substituted.

In the definition of formula I $Ar_1$ represents a diradical derived from a 5- or -6-membered aromatic ring, which ring can optionally comprise 1-3 heteroatoms selected from N, O and S. These diradicals are derived from carbon atoms in the 5-or 6-membered aromatic ring. Examples of such rings are phenyl, oxazole, isoxazole, furazan, thiazole, isothiazole, pyridine, thiadiazole, thiophene, pyrazole, imidazole, pyrazine, pyrimidine and pyridazine. Preferred diradicals $Ar_1$ are derived from phenyl, oxazole, thiazole, pyridine, thiadiazole, thiophene and pyrazole. A specifically preferred diradical $Ar_1$ is 1,3-pyrazolylene.

In the definition of Formula I $Ar_2$ represents a 6-membered aryl ring, which ring can optionally comprise 1-3 nitrogen atoms. Examples of such aryl groups are phenyl, pyridinyl, pyrazinyl, pyrimidinyl, pyridazinyl and triazinyl. Preferred are phenyl and pyridinyl.

The term $(C_{1-4})$alkyl as used in the definition of Formula I means a branched or unbranched alkyl group having 1-4 carbon atoms, like butyl, isobutyl, tertiary butyl, propyl, isopropyl, ethyl and methyl.

In the terms $(C_{1-4})$alkyloxy, $(C_{1-4})$alkyl has the meaning as defined above.

In the term di$(C_{1-4})$alkylamino, each $(C_{1-4})$alkyl group independently has the meaning as defined above.

The term halogen means F, Cl, Br or I.

There is a preference for the 2-(benzimidazol-1-yl)-acetamide bisaryl derivatives of formula I, wherein $Ar_1$ represents 1,3-phenylene, 2,4-thiazolylene, 2,6-pyridinylene, 1,3-pyrazolylene, 3,5-oxazolylene or 1,2,4-thiadiazol-3,5-diyl.

Further preferred are the 2-(benzimidazol-1-yl)-acetamide bisaryl derivatives of formula I wherein $Ar_2$—$Ar_1$— represents 1-phenyl-1H-pyrazol-3-yl, 4-pyridin-2-yl-thiazol-2-yl or 3-phenyl-isoxazol-5-yl.

Specific embodiments of the invention are:
2-benzimidazol-1-yl-N-biphenyl-3-yl-acetamide;
2-benzimidazol-1-yl-N-(2'-methoxy-biphenyl-3-yl)-acetamide;
2-benzimidazol-1-yl-N-(6-methoxy-biphenyl-3-yl)-acetamide;
2-benzimidazol-1-yl-N-(4-methyl-biphenyl-3-yl)-acetamide;
2-benzimidazol-1-yl-N-(4'-chloro-biphenyl-3-yl)-acetamide;
2-benzimidazol-1-yl-N-(4-methoxy-biphenyl-3-yl)-acetamide;
2-benzimidazol-1-yl-N-(2'-methyl-biphenyl-3-yl)-acetamide;
2-benzimidazol-1-yl-N-(6-phenyl-pyridin-2-yl)-acetamide;
2-benzimidazol-1-yl-N-biphenyl-3-ylmethyl-acetamide;
2-benzimidazol-1-yl-N-(4-pyridin-2-yl-thiazol-2-yl)-acetamide;
2-benzimidazol-1-yl-N-(3-phenyl-[1,2,4]thiadiazol-5-yl)-acetamide;
2-benzimidazol-1-yl-N-biphenyl-4-ylmethyl-acetamide;
2-benzimidazol-1-yl-N-biphenyl-2-ylmethyl-acetamide;
2-benzimidazol-1-yl-N-[1-(3-trifluoromethyl-phenyl)-1H-pyrazol-3-yl]-acetamide;
2-benzimidazol-1-yl-N-(1-phenyl-1H-pyrazol-3-yl)-acetamide;
2-benzimidazol-1-yl-N-[1-(4-trifluoromethyl-phenyl)-1H-pyrazol-3-yl]-acetamide;
2-benzimidazol-1-yl-N-[1-(3-methyl-phenyl)-1H-pyrazol-3-yl]-acetamide;
2-benzimidazol-1-yl-N-[1-(3-chloro-4-methyl-phenyl)-1H-pyrazol-3-yl]-acetamide;
2-benzimidazol-1-yl-N-[1-(3,5-difluoro-phenyl)-1H-pyrazol-3-yl]-acetamide;
2-benzimidazol-1-yl-N-[1-(3-fluoro-phenyl)-1H-pyrazol-3-yl]-acetamide;
2-benzimidazol-1-yl-N-[1-(3,4-difluoro-phenyl)-1H-pyrazol-3-yl]-acetamide;
2-benzimidazol-1-yl-N-[3-(6-methyl-pyridin-2-yl)-phenyl]-acetamide;
2-benzimidazol-1-yl-N-(3-m-tolyl-isoxazol-5-yl)-acetamide;
2-benzimidazol-1-yl-N-(2'-chloro-biphenyl-4-yl)-acetamide;
2-benzimidazol-1-yl-N-(3'-chloro-biphenyl-4-yl)-acetamide;
2-benzimidazol-1-yl-N-(3'-methoxy-biphenyl-4-yl)-acetamide;
2-benzimidazol-1-yl-N-(2'-methoxy-biphenyl-4-yl)-acetamide;
2-benzimidazol-1-yl-N-(biphenyl-4-yl)-acetamide;
2-benzimidazol-1-yl-N-(4'-methyl-biphenyl-3-yl)-acetamide;
2-benzimidazol-1-yl-N-(4'-cyano-biphenyl-3-yl)-acetamide;
2-benzimidazol-1-yl-N-(3'-trifluoromethyl-biphenyl-3-yl)-acetamide;
2-benzimidazol-1-yl-N-(3'-cyano-biphenyl-3-yl)-acetamide;
2-benzimidazol-1-yl-N-(4'-methoxy-biphenyl-3-yl)-acetamide;
2-benzimidazol-1-yl-N-[3-(4-methyl-pyridin-2-yl)-phenyl]-acetamide;
2-benzimidazol-1-yl-N-[3-(4-trifluoromethyl-pyrimidin-2-yl)-phenyl]-acetamide;
2-benzimidazol-1-yl-N-(3'-methoxy-biphenyl-3-yl)-acetamide;
2-benzimidazol-1-yl-N-(3'-methyl-biphenyl-3-yl)-acetamide;
2-benzimidazol-1-yl-N-[3-(5-methyl-pyridin-2-yl)-phenyl]-acetamide;
2-benzimidazol-1-yl-N-[3-(5-trifluoromethyl-pyridin-2-yl)-phenyl]-acetamide;
2-benzimidazol-1-yl-N-[3-(6-trifluoromethyl-pyridin-2-yl)-phenyl]-acetamide;
2-benzimidazol-1-yl-N-(3'-trifluoromethoxy-biphenyl-3-yl)-acetamide;
2-benzimidazol-1-yl-N-[3-(4-trifluoromethyl-pyridin-2-yl)-phenyl]-acetamide;
2-benzimidazol-1-yl-N-(4'-methyl-biphenyl-2-ylmethyl)-acetamide;
2-benzimidazol-1-yl-N-(3'-methyl-biphenyl-2-ylmethyl)-acetamide;
2-benzimidazol-1-yl-N-(4'-chloro-biphenyl-2-ylmethyl)-acetamide;
2-benzimidazol-1-yl-N-(3'-chloro-biphenyl-2-ylmethyl)-acetamide;
2-benzimidazol-1-yl-N-(3',4'-difluoro-biphenyl-2-ylmethyl)-acetamide;
2-benzimidazol-1-yl-N-(4'-trifluoromethyl-biphenyl-2-ylmethyl)-acetamide;
2-benzimidazol-1-yl-N-(3'-trifluoromethyl-biphenyl-2-ylmethyl)-acetamide;
2-benzimidazol-1-yl-N-(3'-dimethylamino-biphenyl-2-ylmethyl)-acetamide;
2-benzimidazol-1-yl-N-(2'-methyl-biphenyl-4-ylmethyl)-acetamide;
2-benzimidazol-1-yl-N-(3'-methoxy-biphenyl-4-ylmethyl)-acetamide;
2-benzimidazol-1-yl-N-(2'-trifluoromethyl-biphenyl-4-ylmethyl)-acetamide;
2-benzimidazol-1-yl-N-(3'-trifluoromethyl-biphenyl-4-ylmethyl)-acetamide;
2-benzimidazol-1-yl-N-(2'-dimethylamino-biphenyl-4-ylmethyl)-acetamide;
2-benzimidazol-1-yl-N-(3'-methyl-biphenyl-3-ylmethyl)-acetamide;
2-benzimidazol-1-yl-N-(3'-methoxy-biphenyl-3-ylmethyl)-acetamide;

2-benzimidazol-1-yl-N-(2'-trifluoromethyl-biphenyl-3-ylmethyl)-acetamide;

2-benzimidazol-1-yl-N-(3'-trifluoromethyl-biphenyl-3-ylmethyl)-acetamide;

or a pharmaceutically acceptable salt thereof.

The 2-(benzimidazol-1-yl)-acetamide bisaryl derivatives of the invention can be prepared by methods well known in the art of organic chemistry.

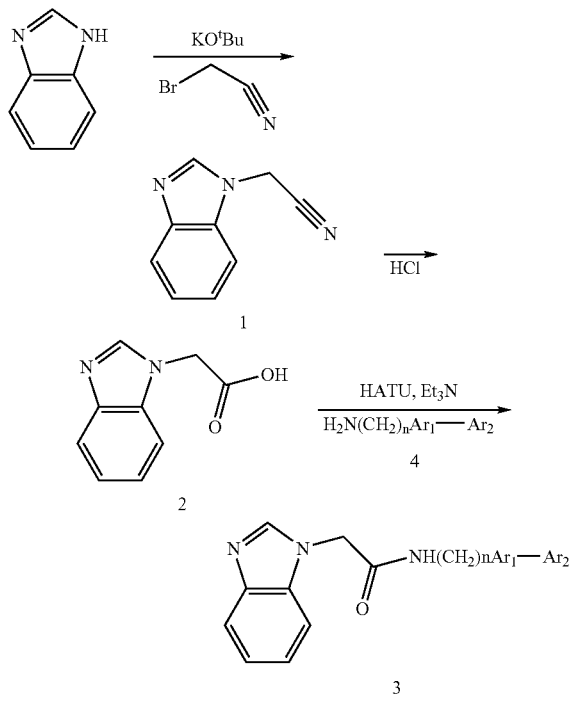

In an illustrative general route to compounds of the present invention, as depicted in Scheme I, the intermediate (1H-benzimidazol-1-yl)acetic acid 2 can be prepared from benzimidazole and a suitable deprotonating base such as potassium tert-butoxide and alkylating with the appropriate nitrile such as bromoacetonitrile in a suitable solvent such as ethanol (J. Das et al. Bioorganic and Medicinal Chemistry Letters 15(2), 337-343, 2005). The nitrile 1 can then be hydrolysed to the desired acid with 18% hydrochloric acid and is well known to someone skilled in the art. Various salt forms of this intermediate can be formed such as the hydrochloride and triethylamine salt. The carboxylic acid of formula 2 or its salt forms (such as hydrochloride or triethylamine) can be converted to amide of formula 3 via its conversion into an activated form i.e. an acyl azide by treatment with diphenylphosphorylazide (DPPA), an acyl chloride by treatment with thionyl chloride or the activated ester by treatment with O-(7-azabenzotriazol-1-yl)-N,N,N',N'-tetramethyluronium hexafluorophosphate (HATU) and further treatment with the appropriate amine $H_2N-(CH_2)_n-Ar_1-Ar_2$ of formula 4 (J. Am. Chem. Soc., Vol. 108, No. 22, 6950-6960, 1986,). Alternative methods of coupling amines of formula 4 to the acid 2 include, but are not limited to the use of peptide coupling reagents such as 1,3-dicylohexylcarbodiimide (DCC), 1,3-diisopropylcarbodiimide (DIC) or bromotripyrrolidinophosphonium hexaflurophosphate (PyBroP). Suitable solvents are aprotic polar solvents such as dimethylformamide (DMF) or acetonitrile although other solvents may be used. Bases such as tertiary amines e.g. triethylamine can be used as well as heteroaromatic bases e.g pyridine. The temperature may be between 0 to 100° C. using either conventional or microwave heating and the reaction time between 1 h and 30 h. The target compounds of formula 3 can exist in various salt forms such as hydrochloride and trifluoroacetic acid salts.

The amine intermediates represented by formula 4 can be prepared using a variety of methods to those skilled in the art, and some are outlined in Scheme II. Boronic acids of formula 5 can undergo Suzuki type coupling to give biaryls of formula 6 as outlined by N-H. Lin et al., Bioorganic and Medicinal Chemistry Letters 11(5), 631-633, 2001. Alpha bromo ketones of formula 7 can be converted to the aminothiazole 8 with thiourea using standard chemistry outlined by J. Brienholt et al., J. Heterocyclic Chemistry 38, 569, 2001. Pyrrozoles of formula 10 can be prepared using the methods outlined in EP 22578, followed by oxidation described by N. Jagerovic et al., Bioorganic and Medicinal Chemistry 10(3), 817-827, 2002.

Scheme II:

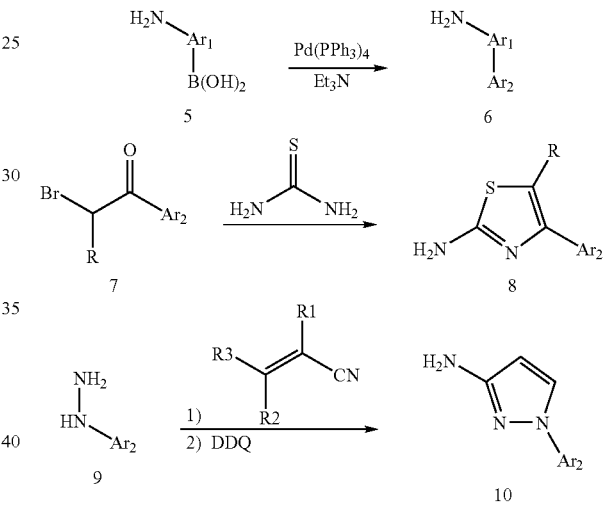

In an alternative method compounds of Formula I of the invention can be obtained using the above mentioned Suzuki coupling reaction of an appropriately halogenated monoaryl derivative of formula 11 with the boronic acid derivative of formula 12.

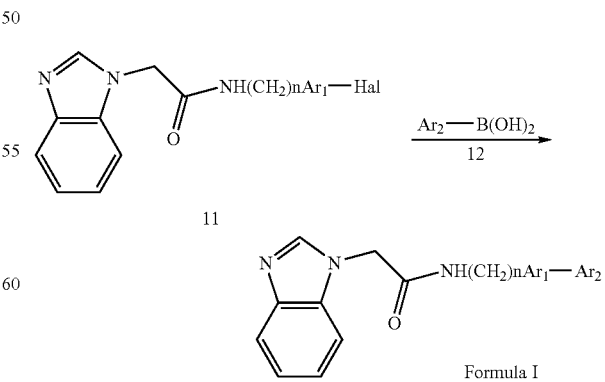

Pharmaceutically acceptable salts of the 2-(benzimidazol-1-yl)-acetamide bisaryl derivatives of the invention may be obtained by treating a free base of a compound of Formula I with a mineral acid such as hydrochloric acid, hydrobromic acid, phosphoric acid and sulfuric acid, or an organic acid such as for example ascorbic acid, citric acid, tartaric acid, lactic acid, maleic acid, malonic acid, fumaric acid, oxalic acid, glycolic acid, succinic acid, propionic acid, acetic acid and methane sulfonic acid.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

Some of the 2-(benzimidazol-1-yl)-acetamide bisaryl derivatives of Formula I and their salts may contain at least one centre of chirality, and exist therefore as stereoisomers, including enantiomers and diastereomers. The present invention includes the aforementioned stereoisomers within its scope and each of the individual R and S enantiomers of the compounds of Formula I and their salts, substantially free, i.e. associated with less than 5%, preferably less than 2%, in particular less than 1% of the other enantiomer, and mixtures of such enantiomers in any proportions including the racemic mixtures containing substantially equal amounts of the two enantiomers.

Methods for asymmetric synthesis or chiral separation whereby the pure stereoisomers are obtained are well known in the art, e.g. synthesis with chiral induction or starting from commercially available chiral substrates, or separation of stereoisomers, for example using chromatography on chiral media or by crystallisation with a chiral counter-ion.

The present invention further provides pharmaceutical compositions comprising a 2-(benzimidazol-1-yl)-acetamide bisaryl derivative according to general Formula I, or a pharmaceutically acceptable salt thereof, in admixture with pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, epidural, intrathecal, intramuscular, transdermal, pulmonary, local, or rectal administration, and the like, all in unit dosage forms for administration.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition, Lippincott Williams & Wilkins, 2000, see especially Part 5: Pharmaceutical Manufacturing), the active agent may be compressed into solid dosage units, such as pills, tablets, or be processed into capsules, suppositories or patches. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The 2-(benzimidazol-1-yl)-acetamide bisaryl derivatives of the invention were found to have antagonistic properties at the vanilloid receptor as measured by a functional calcium influx assay using a Chinese Hamster Ovary cell line in which a human recombinant VR1 receptor had been stably expressed. Methods to construct such recombinant cell lines are well known in the art (Sambrook et al., Molecular Cloning: a Laboratory Manual, Cold Spring Harbor Laboratory Press, Cold Spring Harbor, latest edition).

The compounds of the invention are thus useful in the treatment of TRPV1 mediated disorders, such as in the treatment of acute and chronic pain disorders, acute and chronic neuropathic pain, acute and chronic inflammatory pain, and respiratory diseases. The compounds of the invention may be administered to humans in a sufficient amount and for a sufficient amount of time to alleviate the symptoms. Illustratively, dosage levels for humans can be in the range of 0.001-50 mg per kg body weight, preferably in a dosage of 0.01-20 mg per kg body weight.

The invention is illustrated by the following Examples.

EXAMPLE 1

2-Benzimidazol-1-yl-N-biphenyl-3-yl-acetamide (hydrochloride salt)

A: (1H-benzimidazol-1-yl)acetonitrile

To an ice cooled solution of benzimidazole (10 g, 0.085 mol) in dry N,N-dimethylformamide (500 mL) was added potassium tert-butoxide (9.6 g, 0.085 mol) portionwise. The mixture was stirred at room temperature for 1 h then bromoacetonitrile (6 mL, 0.086 mol) was added in one portion and stirred for 3 h. The mixture was then quenched with solid carbon dioxide followed by water and the organics separated. The organics were washed further with water (100 mL×5), and brine (100 mL×1) combined and dried ($Na_2SO_4$), filtered and evaporated to dryness. The residue was passed through a silica gel column eluting with dichloromethane:ethanol (1% up to 6% ethanol) to give a yellow solid (12 g, 89%). $^1$H NMR (400 MHz, $CDCl_3$) δ ppm 5.08 (2H, s), 7.36-7.43 (2H, m), 7.47 (1H, d, J=7.4 Hz), 7.85 (1H, d, J=7.2 Hz), 7.93 (1H, s).

B: (1H-benzimidazol-1-yl)acetic acid (hydrochloride salt)

(1H-Benzimidazol-1-yl)acetonitrile (35 g, 0.23 mol) (Example 1A) was dissolved in 18% hydrochloric acid (500 mL) and heated to reflux for 5 h. The solution was then evaporated to dryness under reduced pressure using acetonitrile as a co-solvent to azeptropically remove all the solvent. Acetone was added and the solid ($NH_4Cl$) filtered and washed with acetone. The filtrate was then left to stand cool for 24 h and the light brown crystals collected and dried (45 g, 100%). $^1$H NMR (400 MHz, CD$_3$OD) δ ppm 5.47 (2H, s), 7.68-7.70 (2H, m), 7.88-7.92 (2H, m), 9.51 (1H, s). MS (ES) m/z 177.4 [M+H]$^+$.

C: 2-benzimidazol-1-yl-N-biphenyl-3-yl-acetamide (hydrochloride salt)

(1H-Benzimidazol-1-yl)acetic acid (triethylamine salt) (315 mg, 1.1 mmol), O-(7-azabenzotriazol-1-yl)-N,N,N',N'-tetramethyluronium hexaflurophosphate (520 mg, 1.4 mmol), 3-amino biphenyl (290 mg, 1.6 mmol) and triethylamine (0.6 mL, 4.4 mmol) in acetonitrile (10 mL) was stirred at room temperature for 24 h. Methanol (10 mL) was then added and evaporated to dryness in vacuo. The crude mixture was then passed through a silica gel column eluting with ethyl acetate:methanol (1% up to 3% methanol). The product was collected and dried, dissolved in methanol and 1 M hydrogen chloride in diethyl ether (0.5 mL) added and product crystallised, filtered and dried to give the title compound as a white solid (70 mg, 17%). $^1$H NMR (400 MHz, CD$_3$OD+1 drop of DMSO-d$_6$) δ ppm 5.55 (2H, s), 7.32-7.35 (1H, m), 7.40-7.44 (4H, m), 7.56-7.59 (3H, m), 7.67-7.72 (2H, m), 7.89-7.96 (3H, m), 9.54 (1H, s). MS (ES) m/z 327.9 [M+H]$^+$.

The method of Example 1C was further used to prepare the following compounds:

1D: 2-Benzimidazol-1-yl-N-(2'-methoxy-biphenyl-3-yl)-acetamide

Prepared using 2'-methoxy-biphenyl-3-ylamine in place of 3-amino biphenyl. $^1$H NMR (400 MHz, CD$_3$OD) δ ppm 3.77 (3H, s), 5.48 (2H, s), 7.99 (1H, t, J=8 Hz), 7.05 (1H, d, J=8 Hz), 7.24-7.33 (4H, m), 7.56 (1H, d, J=8 Hz), 7.65-7.69 (3H, m), 7.86-7.89 (2H, m), 9.42 (1H, s). MS (ES) m/z: 358.3 [M+H].

1E: 2-Benzimidazol-1-yl-N-(6-methoxy-biphenyl-3-yl)-acetamide

Prepared using 6-methoxy-biphenyl-3-ylamine in place of 3-amino biphenyl. $^1$H NMR (400 MHz, CD$_3$OD) δ ppm 3.77 (3H, s), 5.46 (2H, s), 7.04 (1H, d, J=8 Hz), 7.28-7.55 (7H, m), 7.66-7.68 (2H, m), 7.86-7.89 (2H, m), 9.42 (1H, s). MS (ES) m/z: 358.3 [M+H].

1F: 2-Benzimidazol-1-yl-N-(4-methyl-biphenyl-3-yl)-acetamide

Prepared 1C using 4-methyl-biphenyl-3-ylamine in place of 3-amino biphenyl. $^1$H NMR (400 MHz, CD$_3$OD) δ ppm 2.34 (3H, s), 5.55 (2H, s), 7.38-7.46 (5H, m), 7.56-7.58 (2H, m), 7.60-7.70 (3H, m), 7.86-7.87 (2H, m), 9.35 (1H, s). MS (ES) m/z: 342.1 [M+H].

1G: 2-Benzimidazol-1-yl-N-(4'-chloro-biphenyl-3-yl)-acetamide

Prepared using 4'-chloro-biphenyl-3-ylamine in place of 3-amino biphenyl. $^1$H NMR (400 MHz, CD$_3$OD) δ ppm 5.48 (2H, s), 7.36-7.45 (4H, m), 7.52-7.58 (3H, m), 7.60-7.68 (2H, m), 7.81-7.86 (3H, m), 9.32 (1H, s). MS (ES) m/z: 362.1 [M+H].

1H: 2-Benzimidazol-1-yl-N-(4-methoxy-biphenyl-3-yl)-acetamide

Prepared using 4-methoxy-biphenyl-3-ylamine in place of 3-amino biphenyl. $^1$H NMR (400 MHz, CD$_3$OD) δ ppm 3.98 (3H, s), 5.57 (2H, s), 7.14 (1H, d, J=8 Hz), 7.25 (1H, t, J=8 Hz), 7.35 (2H, t, J=8 Hz), 7.42 (1H, d, J=8 Hz), 7.51 (2H, d, J=8 Hz), 7.65-7.69 (2H, m), 7.86-7.91 (2H, m), 8.28 (1H, s), 9.42 (1H, s). MS (ES) m/z: 358.3 [M+H].

1I: 2-Benzimidazol-1-yl-N-(2'-methyl-biphenyl-3-yl)-acetamide

Prepared using 2'-methyl-biphenyl-3-ylamine in place of 3-amino biphenyl. $^1$H NMR (400 MHz, CD$_3$OD) δ ppm 2.65 (3H, s), 5.46 (2H, s), 7.08 (2H, d, J=8 Hz), 7.14-7.25 (4H, m), 7.39 (1H, t, J=8 Hz), 7.54-7.56 (2H, m), 7.53-7.65 (2H, m), 7.85-7.87 (2H, m), 9.32 (1H, s). MS (ES) m/z: 342.1 [M+H].

EXAMPLE 2

2-Benzimidazol-1-yl-N-(6-phenyl-pyridin-2-yl)-acetamide

To a solution of (1H-benzimidazol-1-yl)acetic acid (1 g, 5.68 mmol) (Example 1B) in N,N-dimethylformamide (25 mL) was added thionyl chloride (0.4 mL, 5.56 mmol) dropwise and the reaction mixture stirred at room temperature for 1 h. 6-Phenyl-pyridin-2-ylamine (5.46 mmol) and pyridine (4 mL) were then added to the reaction mixture and stirred at room temperature for 17 h. The reaction mixture was then concentrated in vacuo and dichloromethane was added and transferred to a separating funnel where the organics were washed with 0.1M hydrochloric acid and 10% ammonium hydroxide solution. The organic layers were combined and washed with saturated aqueous sodium chloride, dried (Mg$_2$SO$_4$), filtered and concentrated in vacuo. The residue was then purified by column chromatography using silica and eluting with 0-10% methanol in dichloromethane, affording the title compound. $^1$H NMR (400 MHz, CD$_3$OD) δ ppm 5.29 (2H, s), 7.28-7.35 (2H, m), 7.39-7.48 (3H, m), 7.54 (1H, d, J=7.2 Hz), 7.62 (1H, d, J=7.7 Hz), 7.71 (1H, d, J=7.3 Hz), 7.81 (1H, t, J=7.9 Hz), 7.98 (1H, br d), 8.05 (2H, d, J=7.3 Hz), 8.23 (1H, s). MS (ES) m/z: 329.1 [M+H].

The method of Example 2 was further used to prepare the following compounds

2A: 2-Benzimidazol-1-yl-N-biphenyl-3-ylmethyl-acetamide (trifluoroacetic acid salt)

Prepared using biphenyl-3-yl-methylamine in place of 6-phenyl-pyridin-2-ylamine. $^1$H NMR (400 MHz, CD$_3$OD) δ ppm 4.52 (2H, s), 5.29 (2H, s), 7.28-7.36 (2H, m), 7.39-7.44 (3H, m), 7.49-7.63 (7H, m), 7.71 (1H, d, J=8.2 Hz), 7.83 (1H, d, J=8.1 Hz), 9.19 (1H, s). MS (ES) m/z: 342.0 [M+H].

2B: 2-Benzimidazol-1-yl-N-(4-pyridin-2-yl-thiazol-2-yl)-acetamide

Prepared using 4-pyridin-2-yl-thiazol-2-ylamine in place of 6-phenyl-pyridin-2-ylamine. $^1$H NMR (400 MHz, CD$_3$OD) δ ppm 5.33 (2H, s), 7.29-7.36 (3H, m), 7.52 (1H, d, J=7.1 Hz), 7.71 (1H, d, J=7.1 Hz), 7.76 (1H, s), 7.85-7.90 (1H, m), 8.08 (1H, d, J=7.9 Hz), 8.24 (1H, s), 8.55 (1H, d, J=4.9 Hz). MS (ES) m/z: 336.1 [M+H].

2C: 2-Benzimidazol-1-yl-N-(3-phenyl-[1,2,4]thiadiazol-5-yl)-acetamide

Prepared using 3-phenyl-[1,2,4]thiadiazol-5-ylamine in place of 6-phenyl-pyridin-2-ylamine. $^1$H NMR (400 MHz, CD$_3$OD) δ ppm 5.34 (2H, s), 7.30-7.36 (2H, m), 7.44-7.46 (3H, m), 7.52 (1H, d, J=6.9 Hz), 7.72 (1H, d, J=7.0 Hz), 8.22-8.23 (3H, m). MS (ES) m/z: 336.1 [M+H].

2D: 2-Benzimidazol-1-yl-N-biphenyl-4-ylmethyl-acetamide

Prepared using biphenyl-4-yl-methylamine in place of 6-phenyl-pyridin-2-ylamine. $^1$H NMR (400 MHz, CD$_3$OD) δ ppm 4.49 (2H, s), 5.24 (2H, s), 7.30-7.49 (5H, m), 7.52-7.60 (5H, m), 7.75-7.79 (1H, m), 7.81-7.89 (2H, m), 9.42 (1H, s). MS (ES) m/z: 342.1 [M+H].

2E: 2-Benzimidazol-1-yl-N-biphenyl-2-ylmethyl-acetamide

Prepared using biphenyl-2-yl-methylamine in place of 6-phenyl-pyridin-2-ylamine. $^1$H NMR (400 MHz, CD$_3$OD) δ ppm 4.39 (2H, s), 5.19 (2H, s), 7.20-7.22 (1H, m), 7.30-7.49 (8H, m), 7.60-7.62 (2H, m), 7.65-7.70 (1H, m), 7.80-7.83 (1H, m), 9.22 (1H, s). MS (ES) m/z: 342.1 [M+H].

EXAMPLE 3

2-Benzimidazol-1-yl-N-[1-(3-trifluoromethyl-phenyl)-1H-pyrazol-3-yl]-acetamide

A: 1-(3-trifluoromethyl-phenyl)-4,5-dihydro-1H-pyrazol-3-ylamine (hydrochloride salt)

Sodium ethoxide (3.9 g, 0.056 mmol) dissolved in ethanol (100 mL) and 3-(trifluoromethyl) phenylhydrazine (5 g, 0.028 mol) added followed by acrylonitrile (2.3 mL, 0.035 mol) and heated to reflux for 24 h. The solution was then evaporated to dryness in vacuo and water added. The solution was then extracted into dichloromethane and the organics combined, dried (Na$_2$SO$_4$), filtered and evaporated to dryness. The residue was then passed through a silica gel column eluting with dichloromethane:methanol. Product fractions collected and evaporated to dryness, dissolved in dichloromethane and 1M hydrogen chloride in diethyl ether added to form a white solid which was collected by filtration and dried (3 g, 40%). $^1$H NMR (400 MHz, CD$_3$OD) δ ppm 3.23 (2H, br m), 4.04 (2H, br m), 7.32-7.37 (3H, br m), 7.56 (1H, br s). MS (ES) m/z: 230.0 [M+H].

B: 1-(3-trifluoromethyl-phenyl)-1H-pyrazol-3-ylamine (hydrochloride salt)

To a solution of 1-(3-trifluoromethyl-phenyl)-4,5-dihydro-1H-pyrazol-3-ylamine hydrochloride salt (200 mg, 0.88 mmol) (Example 3A) in dioxane (50 mL) was added triethylamine (0.069 mL, 0.88 mmol) followed by 2,3-dichloro-5,6-dicyano-p-benzoquinone (DDQ) (200 mg, 0.88 mmol). The mixture was stirred at room temperature for 24 h and then poured onto dichloromethane. 2N hydrochloric acid was added and the organics extracted with 2N hydrochloric acid (3×50 mL). The acid layer was basified with 10N potassium hydroxide and extracted with dichloromethane (3×50 mL). The combined organics were dried (Na$_2$SO$_4$), filtered and evaporated to dryness. The residue dissolved in diethyl ether and 1M hydrochloric acid in diethyl ether was added to form a brown solid which was collected and dried (171 mg, 86%). MS (ES) m/z: 228.1 [M+H].

C: 2-benzimidazol-1-yl-N-[1-(3-trifluoromethyl-phenyl)-1H-pyrazol-3-yl]-acetamide Prepared following the method in Example 2 using 1-(3-trifluoromethyl-phenyl)-1H-pyrazol-3-ylamine (Example 3B) in place of 2-amino-4-(4-chlorophenyl)thiazole. The residue was then purified by preparative LCMS affording title compound. $^1$H NMR (400 MHz, CDCl$_3$) δ ppm 5.03 (2H, s), 7.01 (1H, d, J=2.4 Hz), 7.25 (2H, s), 7.36-7.43 (3H, m), 7.48-7.54 (2H, m), 7.69 (1H, d, J=7.5 Hz), 7.80 (1H, s), 8.85 (1H, d, J=2.5 Hz), 7.88-7.93 (2H, m), 8.02 (1H, s). MS (ES) m/z: 386.3.0 [M+H].

The method of Example 3 was further used to prepare the following compounds:

3D: 2-Benzimidazol-1-yl-N-(1-phenyl-1H-pyrazol-3-yl)-acetamide $^1$H NMR (400 MHz, DMSO-d$_6$) δ ppm 5.37 (2H, s), 6.71 (1H, s), 7.29-7.31 (1H, m), 7.43-7.52 (4H, m), 7.75-7.80 (4H, m), 8.41 (1H, s), 8.94 (1H, s). MS (ES) m/z: 318.0 [M+H].

3E: 2-Benzimidazol-1-yl-N-[1-(4-trifluoromethyl-phenyl)-1H-pyrazol-3-yl]-acetamide $^1$H NMR (400 MHz, DMSO-d$_6$) δ ppm 5.39 (2H, s), 6.79 (1H, s), 7.40-7.50 (2H, m), 7.79 (2H, t, J=8 Hz), 7.88 (2H, d, J=8 Hz), 8.81 (2H, d, J=8 Hz), 8.58 (1H, s), 9.00 (1H, s), 11.35 (1H, s). MS (ES) m/z: 386.4 [M+H].

3F: 2-Benzimidazol-1-yl-N-[1-(3-methyl-phenyl)-1H-pyrazol-3-yl]-acetamide $^1$H NMR (400 MHz, DMSO-d$_6$) δ ppm 2.38 (3H, s), 5.35 (2H, s), 6.69 (1H, s), 7.10 (1H, d, J=8 Hz), 7.36 (1H, t, J=8 Hz), 7.37-7.48 (2H, m), 7.58 (1H, d, J=8 Hz), 7.63 (1H, s), 7.73-7.81 (2H, m), 8.38 (1H, s), 8.95 (1H, s), 11.30 (1H, s). MS (ES) m/z: 332.4 [M+H].

3G: 2-Benzimidazol-1-yl-N-[1-(3-chloro-4-methyl-phenyl)-1H-pyrazol-3-yl]-acetamide $^1$H NMR (400 MHz, DMSO-d$_6$) δ ppm 2.35 (3H, s), 5.35 (2H, s), 6.71 (1H, s), 7.40-7.48 (3H, m), 7.68 (1H, d, J=8 Hz), 7.73-7.80 (2H, m), 7.86 (1H, s), 7.48 (1H, s), 8.91 (1H, s), 11.30 (1H, s). MS (ES) m/z: 366.2 [M+H].

3H: 2-Benzimidazol-1-yl-N-[1-(3,5-difluoro-phenyl)-1H-pyrazol-3-yl]-acetamide $^1$H NMR (400 MHz, DMSO-d$_6$) δ ppm 5.35 (2H, s), 6.78 (1H, s), 7.15-7.18 (1H, m), 7.40-7.45 (2H, m), 7.56 (2H, d, J=8 Hz), 7.74 (1H, d, J=8 Hz), 7.78 (1H, d, J=8 Hz), 8.56 (1H, s), 8.89 (1H, s), 11.20 (1H, s). MS (ES) m/z: 354.3 [M+H].

3I: 2-Benzimidazol-1-yl-N-[1-(3-fluoro-phenyl)-1H-pyrazol-3-yl]-acetamide $^1$H NMR (400 MHz, DMSO-d$_6$) δ ppm 5.29 (2H, s), 6.75 (1H, s), 7.12 (1H, t, J=8 Hz), 7.32-7.40 (2H, m), 7.55-7.57 (2H, m), 7.63-7.65 (3H, m), 7.75 (1H, d, J=8 Hz), 8.50 (1H, s), 8.60 (1H, s), 11.30 (1H, s). MS (ES) m/z: 336.2 [M+H].

3J: 2-Benzimidazol-1-yl-N-[1-(3,4-difluoro-phenyl)-1H-pyrazol-3-yl]-acetamide $^1$H NMR (400 MHz, DMSO-d$_6$) δ ppm 5.30 (2H, s), 6.75 (1H, s), 7.30-7.37 (2H, m), 7.58-7.68 (3H, m), 7.75 (1H, d, J=8 Hz), 7.85-7.90 (1H, m), 8.48 (1H, s), 8.65 (1H, s), 11.30 (1H, s). MS (ES) m/z: 354.3 [M+H].

EXAMPLE 4

2-Benzimidazol-1-yl-N-[3-(6-methyl-pyridin-2-yl)-phenyl]-acetamide (trifluoroacetic acid salt)

A: 3-(6-methyl-pyridin-2-yl)-phenylamine

2-Bromo-6-methylpyridine (392 mg, 2.27 mmol) 3-aminophenylboronic acid (374 mg, 2.73 mmol) and tetrakis(triphenylphosphine)palladium (131 mg, 0.11 mmol) in ethanol (4 mL) and triethylamine (0.634 mL, 4.54 mmol) was heated to 150° C. for 600 s in a Emrys optimizer EXP microwave. The mixture was then evaporate to dryness and passed through a silica gel column eluting with heptane:ethyl acetate (1:1) to give the product as a brown solid (60 mg, 12%). $^1$H NMR (400 MHz, CDCl$_3$) δ ppm 2.61 (3H, s), 3.73 (2H, br s), 6.71-6.73 (1H, m), 7.07 (1H, d, J=7.6 Hz), 7.21-7.25 (1H, m), 7.31 (1H, d, J=7.8 Hz), 7.36 (1H, s), 7.47 (1H, d, J=7.8 Hz), 7.59 (1H, t, J=7.7 Hz). MS (ES) m/z: 174.3 [M+H].

B: 2-benzimidazol-1-yl-N-[3-(6-methyl-pyridin-2-yl)-phenyl]-acetamide (trifluoroacetic acid salt).

Prepared following the method in Example 1C using 3-(6-methyl-pyridin-2-yl)-phenylamine (Example 7A) in place of 3-amino biphenyl. The residue was then purified by preparative HPLC affording title compound. $^1$H NMR (400 MHz, CD$_3$OD) δ ppm 2.82 (3H, s), 5.58 (2H, s), 7.61-7.69 (4H, m), 7.77-7.81 (1H, m), 7.89-7.93 (2H, m), 8.00 (1H, d, J=7.9 Hz), 8.26 (1H, s), 8.42 (1H, t, J=7.9 Hz), 9.49 (1H, s). MS (ES) m/z: 343.3 [M+H].

EXAMPLE 5

2-Benzimidazol-1-yl-N-(3-m-tolyl-isoxazol-5-yl)-acetamide (1H-Benzimidazol-1-yl)acetic acid (50 mg, 0.28 mmol) (Example 1B) suspended in dichloromethane (5 mL) and diisopropylethylamine (0.19 mL, 1.12 mmol) and stirred for 1 h at room temperature until a clear solution was observed. 3-m-Tolyl-isoxazol-5-yl amine (53 mg, 0.28 mmol) and bromotripyrrolidinophosphonium hexaflurophosphate (PyBroP) (130 mg, 0.28 mmol) were then added and stirred for 24 h at room temperature. Sodium carbonate was then added and the mixture passed through a hydrophobic frit. The organic layer was collected and evaporated to dryness. The residue was then purified by preparative HPLC affording title compound 1 mg. $^1$H NMR (400 MHz, DMSO-d$_6$) δ ppm 2.34 (3H, s), 5.07 (2H, s), 6.50 (1H, s), 7.17-7.24 (3H, m), 7.33 (1H, t, J=7.6 Hz), 7.52 (2H, t, J=8.6 Hz), 7.57 (1H, s), 7.65 (1H, d, J=7.2 Hz), 8.18 (1H, s). MS (ES) m/z: 333.1 [M+H].

EXAMPLE 6

2-Benzimidazol-1-yl-N-(2'-chloro-biphenyl-4-yl)-acetamide

A: 2-benzimidazol-1-yl-N-(4-bromophenyl)-acetamide

2-Bromo-N-(4-bromophenyl)-acetamide (3.083 g, 10.522 mmol), prepared according to *J. Med. Chem.*, 1996, 4(2), 197-203, benzimidazole (1.24 g, 10.52 mmol) and K$_2$CO$_3$ were combined and dissolved in DMF (60 mL) under nitrogen. The reaction mixture was stirred at room temperature overnight before filtering and purifing by SCX cartridge. The crude product thus obtained was washed with EtOAc to remove excess benzimidazole, yielding the pure product (2.20 g, 63% yield). $^1$H NMR (400 MHz, DMSO-d$_6$) δ ppm 5.17 (2H, s), 7.19-7.28 (2H, m), 7.51 (2H, d, J=12 Hz), 7.51-7.56 (1H, m), 7.57 (2H, d, J=12 Hz), 7.66 (1H, d, J=8 Hz), 8.22 (1H, s), 10.57 (1H, s). MS (ES) m/z: 332.5 [M+H].

B: 2-benzimidazol-1-yl-N-(2'-chloro-biphenyl-4-yl)-acetamide

2-Benzimidazol-1-yl-N-(4-bromophenyl)-acetamide (100 mg, 0.30 mmol) (Example 6A), PdCl$_2$(PPh$_3$)$_2$ (22 mg, 0.03 mmol), K$_2$CO$_3$ (120 mg, 0.8 mmol) and 2-chlorophenylboronic acid (71 mg, 0.45 mmol) were combined and dissolved in DME (0.5 mL), EtOH (0.5 mL) and H$_2$O (0.2 mL). This mixture was heated in a microwave at 110° C. for 10 minutes. SCX purification of the reaction mixture, followed by further purification using prep LCMS yielded the desired product (34 mg). $^1$H NMR (400 MHz, DMSO-d$_6$) δ ppm 5.21 (2H, s), 7.2-7.3 (2H, m), 7.36-7.45 (5H, m), 7.55 (2H, d, J=8 Hz), 7.67-7.72 (3H, m), 8.25 (1H, s), 10.59 (1H, s). MS (ES) m/z: 362.3 [M+H].

The method of Example 6B was further used to prepare the following compounds:

6C: 2-Benzimidazol-1-yl-N-(3'-chloro-biphenyl-4-yl)-acetamide

The preparation used 3-chlorophenylboronic acid (71 mg, 0.453 mmol) in place of 2-chlorophenylboronic acid, yielding the product (30 mg). $^1$H NMR (400 MHz, DMSO-d$_6$) δ ppm 5.21 (2H, s), 7.20-7.28 (2H, m), 7.37-7.40 (1H, m), 7.46 (1H, t, J=8 Hz), 7.55 (1H, d, J=8 Hz), 7.62 (1H, d, J=8 Hz), 7.70 (6H, s), 8.24 (1h, s), 10.6 (1H, s). MS (ES) m/z: 362.3 [M+H].

6D: 2-Benzimidazol-1-yl-N-(3'-methoxy-biphenyl-4-yl)-acetamide

The preparation used 3-methoxyphenylboronic acid (69 mg, 0.453 mmol) in place of 2-chlorophenylboronic acid, yielding the product (11 mg). $^1$H NMR (400 MHz, DMSO-d$_6$) δ ppm 3.81 (3H, s), 5.20 (2H, s), 6.90 (1H, dd, J=2, 7 Hz), 7.17 (1H, s), 7.18-7.29 (3H, m), 7.35 (1H, t, J=8 Hz), 7.55 (1H, d, J=8 Hz), 7.63-7.71 (5h, m), 8.24 (1H, s), 10.56 (1H, s). MS (ES) m/z: 358.3 [M+H].

6E: 2-Benzimidazol-1-yl-N-(2'-methoxy-biphenyl-4-yl)-acetamide

The preparation used 2-methoxyphenylboronic acid (69 mg, 0.453 mmol) in place of 2-chlorophenylboronic acid, yielding the product (45 mg). $^1$H NMR (400 MHz, DMSO-d$_6$) δ ppm 3.75 (3H, s), 5.19 (2H, s), 7.01 (1H, t, J=8 Hz), 7.08 (1H, d, J=8 Hz), 7.19-7.34 (4H, m), 7.44 (2H, d, J=8 Hz), 7.54 (1H, d, J=8 Hz), 7.62 (2H, d, J =8Hz), 7.68 (1H, d, J=8 Hz), 8.25 (1H, s), 10.52 (1H, s). MS (ES) m/z: 358.3 [M+H].

6F: 2-Benzimidazol-1-yl-N-(biphenyl-4-yl)-acetamide

The preparation used Pd(PPh$_3$)$_4$ (18 mg, 0.0151 mmol) and phenylboronic acid (55 mg, 0.453 mmol) in place of PdCl$_2$(PPh$_3$)$_2$ and 2-chlorophenylboronic acid respectively, yielding the product (9 mg). $^1$H NMR (400 MHz, DMSO-d$_6$) δ ppm 5.20 (2H, s), 7.19-7.29 (2H, m), 7.33 (1H, t, J=8 Hz), 7.44 (3H, t, J=8 Hz), 7.55 (1H, d, J=8 Hz), 7.62-7.72 (6H, m), 8.24 (1H, s), 10.55 (1H, s). MS (ES) m/z: 328.1 [M+H].

EXAMPLE 7

2-Benzimidazol-1-yl-N-(4'-methyl-biphenyl-3-yl)-acetamide

A: 4'-methyl-3-nitro-biphenyl

Under an inert atmosphere was added 3-nitrobenzene boronic acid (6.3 mmol) and sodium carbonate (11.6 mmol) to water (8 mL), toluene (8 mL) and ethanol (8 mL) and stirred for 5 minutes. p-Bromotoluene (5.8 mmol) and tetrakis(triphenylphosphine)palladium (0.3 mmol) added and heated to 70° C. for 7 hours. Concentrated under reduced pressure and extracted into chloroform (3×20 mL). The organics were then washed with 10% sodium bicarbonate (10 mL), water (10 mL) and brine (10 mL) before drying over sodium sulfate, filtering and evaporating to dryness. The residue was then purified by column chromatography and taken onto the next stage.

B: 4'-methyl-biphenyl-3-ylamine

4'-Methyl-3-nitro-biphenyl (1.9 g) dissolved in isopropyl alcohol (30 mL) and iron (III) chloride (0.19 g) added followed by charcoal (0.19 g). Mixture heated to 65° C. before adding hydrazine hydrate (7.6 mL) slowly for 45 minutes under nitrogen. Mixture stirred for a further 2 hours at 70° C. Mixture filtered and washed with ethyl acetate. Organics combined and washed with water (50 mL) and brine (50 mL) before drying over sodium sulfate, filtering and evaporating to dryness to leave a yellow solid (1.55 g, 95%).

C: 2-benzimidazol-1-yl-N-(4'-methyl-biphenyl-3-yl)-acetamide

Prepared following the method in Example 1C. The residue was then purified by preparative LCMS affording title compound. $^1$H NMR (400 MHz, DMSO-d$_6$) δ ppm 2.33 (3H, s), 5.36 (2H, s), 7.27 (2H, d, J=8 Hz), 7.35-7.54 (7H, m), 7.80 (2H, t, J=8 Hz), 7.91 (1H, s), 8.97 (1H, s), 10.60 (1H, s). MS (ES) m/z: 344.2 [M+H].

The method of Example 7 was further used to prepare the following compounds:

7D: 2-Benzimidazol-1-yl-N-(4'-cyano-biphenyl-3-yl)-acetamide $^1$H NMR (400 MHz, DMSO-d$_6$) δ ppm 5.32 (2H, s), 7.32-7.39 (2H, m), 7.47-7.49 (2H, m), 7.61-7.63 (1H, m), 7.71 (1H, d, J=8 Hz), 7.73 (1H, d, J=8 Hz), 7.81 (2H, d, J=8 Hz), 7.92 (2H, d, J=8 Hz), 8.03 (1H, s), 8.72 (1H, s), 10.70 (1H, s). MS (ES) m/z: 353.2 [M+H].

7E: 2-Benzimidazol-1-yl-N-(3'-trifluoromethyl-biphenyl-3-yl)-acetamide $^1$H NMR (400 MHz, DMSO-d$_6$) δ ppm 5.31 (2H, s), 7.30-7.33 (2H, m), 7.48 (2H, d, J=4 Hz), 7.61-7.63 (1H, m), 7.68-7.79 (4H, m), 7.87 (1H, s), 7.92 (1H, d, J=8 Hz), 7.98 (1H, s), 8.68 (1H, s), 10.70 (1H, s). MS (ES) m/z: 396.2 [M+H].

7F: 2-Benzimidazol-1-yl-N-(3'-cyano-biphenyl-3-yl)-acetamide $^1$H NMR (400 MHz, DMSO-d$_6$) δ ppm 5.33 (2H, s), 7.32-7.41 (2H, m), 7.47 (2H, d, J=7 Hz), 7.58-7.60 (1H, m), 7.63-7.73 (3H, m), 7.75 (1H, d, J=8 Hz), 7.82 (1H, d, J=8 Hz), 7.90 (1H, d, J=8 Hz), 7.98 (1H, s), 8.05 (1H, s), 8.75 (1H, s), 10.60 (1H, s). MS (ES) m/z: 353.2 [M+H].

7G: 2-Benzimidazol-1-yl-N-(4'-methoxy-biphenyl-3-yl)-acetamide $^1$H NMR (400 MHz, DMSO-d$_6$) δ ppm 3.78 (3H, s), 5.32 (2H, s), 7.01 (2H, d, J=8 Hz), 7.32-7.41 (4H, m), 7.49-7.54 (3H, m), 7.70 (1H, d, J=8 Hz), 7.75 (1H, d, J=8 Hz), 7.89 (1H, s), 8.78 (1H, s), 10.60 (1H, s). MS (ES) m/z: 358.2 [M+H].

7H: 2-Benzimidazol-1-yl-N-[3-(4-methyl-pyridin-2-yl)-phenyl]-acetamide $^1$H NMR (400 MHz, DMSO-d$_6$) δ ppm 2.38 (3H, s), 5.20 (2H, s), 7.17-7.28 (3H, m), 7.43 (1H, t, J=8 Hz), 7.55 (1H, d, J=8 Hz), 7.65-7.70 (3H, m), 7.78 (1H, d, J=8 Hz), 8.25 (1H, s), 8.36 (1H, s), 8.50 (1H, d, J=4 Hz), 10.60 (1H, s). MS (ES) m/z: 343.2 [M+H], 172.2.

7I: 2-Benzimidazol-1-yl-N-[3-(4-trifluoromethyl-pyrimidin-2-yl)-phenyl]-acetamide $^1$H NMR (400 MHz, DMSO-d$_6$) δ ppm 5.35 (2H, s), 7.36-7.42 (2H, m), 7.55 (1H, t, J=8 Hz), 7.72-7.79 (2H, m), 7.88 (1H, d, J=8 Hz), 7.98 (1H, d, J=6 Hz), 8.17 (1H, d, J=8 Hz), 8.67 (1H, s), 8.81 (1H, s), 9.27 (1H, d, J=8 Hz), 10.90 (1H, s). MS (ES) m/z: 398.2 [M+H].

7J: 2-Benzimidazol-1-yl-N-(3'-methoxy-biphenyl-3-yl)-acetamide $^1$H NMR (400 MHz, DMSO-d$_6$) δ ppm 3.81 (3H, s), 5.38 (2H, s), 6.94 (1H, t, J=12 Hz), 7.12 (1H, s), 7.16 (1H, d, J=12 Hz), 7.37-7.45 (5H, m), 7.58 (1H, d, J=8 Hz), 7.72 (1H, d, J=8 Hz), 7.78 (1H, d, J=8 Hz), 7.90 (1H, s), 8.80 (1H, s), 11.00 (1H, s). MS (ES) m/z: 358.2 [M+H].

7K: 2-Benzimidazol-1-yl-N-(3'-methyl-biphenyl-3-yl)-acetamide $^1$H NMR (400 MHz, DMSO-d$_6$) δ ppm 2.36 (3H, s), 5.33 (2H, s), 7.19 (1H, t, J=8 Hz), 7.31-7.43 (7H, m), 7.55 (1H, d, J=8 Hz), 7.71 (1H, d, J=8 Hz), 7.77 (1H, d, J=8 Hz), 7.92 (1H, s), 8.75 (1H, s), 10.60 (1H, s). MS (ES) m/z: 342.2 [M+H].

7L: 2-Benzimidazol-1-yl-N-[3-(5-methyl-pyridin-2-yl)-phenyl]-acetamide $^1$H NMR (400 MHz, DMSO-d$_6$) δ ppm 2.33 (3H, s), 5.32 (2H, s), 7.35-7.45 (3H, m), 7.62-7.80 (6H, m), 8.38 (1H, s), 8.49 (1H, s), 8.77 (1H, s), 10.60 (1H, s). MS (ES) m/z: 343.2 [M+H].

7M: 2-Benzimidazol-1-yl-N-[3-(5-trifluoromethyl-pyridin-2-yl)-phenyl]-acetamide $^1$H NMR (400 MHz, DMSO-d$_6$) δ ppm 5.34 (2H, s), 7.33-7.41 (2H, m), 7.53 (1H, t, J=7.6 Hz), 7.71-7.76 (3H, m), 7.88 (1H, d, J=8 Hz), 8.02 (1H, d, J=8 Hz), 8.30 (1H, d, J=8 Hz), 8.50 (1H, s), 8.77 (1H, s), 9.02 (1H, s). MS (ES) m/z: 397.2 [M+H], 199.2.

7N: 2-Benzimidazol-1-yl-N-[3-(6-trifluoromethyl-pyridin-2-yl)-phenyl]-acetamide $^1$H NMR (400 MHz, DMSO-d$_6$) δ ppm 5.33 (2H, s), 7.35-7.38 (2H, m), 7.50 (1H, t, J=8 Hz), 7.73 (1H, d, J=8 Hz), 7.75 (1H, d, J=8 Hz), 7.80-7.90 (3H, m), 8.18-8.25 (2H, m), 8.36 (1H, s), 8.75 (1H, s). MS (ES) m/z: 397.2 [M+H].

7O: 2-Benzimidazol-1-yl-N-(3'-trifluoromethoxy-biphenyl-3-yl)-acetamide $^1$H NMR (400 MHz, DMSO-d$_6$) δ ppm 5.21 (2H, s), 7.19-7.26 (2H, m), 7.38-7.48 (3H, m), 7.54-7.69 (6H, m), 7.95 (1H, s), 8.24 (1H, s). MS (ES) m/z: 412.2 [M+H].

7P: 2-Benzimidazol-1-yl-N-[3-(4-trifluoromethyl-pyridin-2-yl)-phenyl]-acetamide $^1$H NMR (400 MHz, DMSO-d$_6$) δ ppm 5.36 (2H, s), 7.40-7.46 (2H, m), 7.50 (1H, t, J=8 Hz), 7.73-7.81 (4H, m), 7.90 (1H, d, J=8 Hz), 7.20 (1H, s), 8.46 (1H, s), 8.90 (1H, s), 8.95 (1H, d, J=6 Hz). MS (ES) m/z: 397.2 [M+H], 199.2.

EXAMPLE 8

2-Benzimidazol-1-yl-N-(4'-methyl-biphenyl-2-ylmethyl)-acetamide

A: 4'-methyl-biphenyl-2-carbonitrile

Prepared following the method in Example 7A. The residue was then purified by column chromatography and taken onto next stage.

B: (4'-methyl-biphenyl-2-yl)-methylamine

Lithium aluminium hydride (70 mg) was suspended in dry THF (25 mL). 4'-Methyl-biphenyl-2-carbonitrile (200 mg) was then added in THF (25 mL) to the reaction mixture and heated to 65° C. for 1 hour. The mixture was then cooled and quenched with 10% sodium hydroxide and evaporated to a low volume. The residue was dissolved in ethyl acetate (50 mL) and washed with sodium bicarbonate (20 mL), water (20 mL) and brine (20 mL). The combined organics were dried over sodium sulfate, filtered and evaporated to dryness (61%).

C: 2-benzimidazol-1-yl-N-(4'-methyl-biphenyl-2-ylmethyl)-acetamide

Prepared following the method in Example 1C. The residue was then purified by preparative LCMS affording title compound. $^1$H NMR (400 MHz, DMSO-d$_6$) δ ppm 2.34 (3H, s), 4.24 (2H, d, J=8 Hz), 5.06 (2H, s), 7.20-7.23 (5H, m), 7.34-7.42 (5H, m), 7.56 (1H, d, J=8 Hz), 7.72 (1H, d, J=8 Hz), 8.58 (1H, s), 8.76 (1H, m). MS (ES) m/z: 356.2 [M+H].

The method of Example 8 was further used to prepare the following compounds:

8D: 2-Benzimidazol-1-yl-N-(3'-methyl-biphenyl-2-ylmethyl)-acetamide $^1$H NMR (400 MHz, DMSO-d$_6$) δ ppm 2.33 (3H, s), 4.23 (2H, d, J=8 Hz), 5.06 (2H, s), 7.13-7.28 (4H, m), 7.28-7.42 (6H, m), 7.55 (1H, d, J=8 Hz), 7.72 (1H, d, J=8 Hz), 8.55 (1H, s), 8.76 (1H, m). MS (ES) m/z: 356.2 [M+H].

8E: 2-Benzimidazol-1-yl-N-(4'-chloro-biphenyl-2-ylmethyl)-acetamide $^1$H NMR (400 MHz, DMSO-d$_6$) δ ppm 4.23 (2H, d, J=8 Hz), 5.07 (2H, s), 7.22 (1H, d, J=8 Hz), 7.36-7.48 (8H, m), 7.52 (1H, d, J=8 Hz), 7.75 (1H, d, J=8 Hz), 8.68 (1H, s), 8.80 (1H, m). MS (ES) m/z: 376.2 [M+H].

8F: 2-Benzimidazol-1-yl-N-(3'-chloro-biphenyl-2-ylmethyl)-acetamide $^1$H NMR (400 MHz, DMSO-d$_6$) δ ppm 4.24 (2H, d, J=8 Hz), 5.08 (2H, s), 7.25 (1H, d, J=8 Hz), 7.30-7.49 (8H, m), 7.55 (1H, d, J=8 Hz), 7.75 (1H, d, J=8 Hz), 8.70 (1H, s), 8.80 (1H, m). MS (ES) m/z: 376.2 [M+H].

8G: 2-Benzimidazol-1-yl-N-(3',4'-difluoro-biphenyl-2-ylmethyl)-acetamide $^1$H NMR (400 MHz, DMSO-d$_6$) δ ppm 4.24 (2H, d, J=4 Hz), 5.04 (2H, s), 7.15-7.20 (1H, m), 7.24 (1H, d, J=8 Hz), 7.32-7.53 (8H, m), 7.22 (1H, d, J=8 Hz), 8.54 (1H, s), 8.77 (1H, m). MS (ES) m/z: 378.2 [M+H].

8H: 2-Benzimidazol-1-yl-N-(4'-trifluoromethyl-biphenyl-2-ylmethyl)-acetamide $^1$H NMR (400 MHz, DMSO-d$_6$) δ ppm 4.23 (2H, d, J=4 Hz), 5.07 (2H, s), 7.26 (1H, d, J=8 Hz), 7.33-7.50 (5H, m), 7.56-7.62 (3H, m), 7.71-7.78 (3H, m), 8.65 (1H, s), 8.82 (1H, m). MS (ES) m/z: 410.4 [M+H].

8I: 2-Benzimidazol-1-yl-N-(3'-trifluoromethyl-biphenyl-2-ylmethyl)-acetamide $^1$H NMR (400 MHz, DMSO-d$_6$) δ ppm 4.23 (2H, d, J=8 Hz), 5.05 (2H, s), 7.30-7.53 (7H, m), 7.68-7.75 (5H, m), 8.61 (1H, s), 8.72 (1H, m). MS (ES) m/z: 410.4 [M+H].

8J: 2-Benzimidazol-1-yl-N-(3'-dimethylamino-biphenyl-2-ylmethyl)-acetamide $^1$H NMR (400 MHz, DMSO-d$_6$) δ ppm 2.50 (6H, s), 4.25 (2H, d, J=4 Hz), 5.06 (2H, s), 6.62-6.63 (2H, m), 6.63 (1H, d, J=8 Hz), 7.22-7.25 (2H, m), 7.33-7.37 (5H, m), 7.55 (1H, d, J=8 Hz), 7.72 (1H, d, J=8 Hz), 8.59 (1H, s), 8.75 (1H, m). MS (ES) m/z: 385.2 [M+H], 193.2.

8K: 2-Benzimidazol-1-yl-N-(2'-methyl-biphenyl-4-ylmethyl)-acetamide $^1$H NMR (400 MHz, DMSO-d$_6$) δ ppm 2.23 (3H, s), 4.36 (2H, d, J=8 Hz), 5.06 (2H, s), 7.16-7.36 (10H, m), 7.48 (1H, d, J=8 Hz), 7.66 (1H, d, J=8 Hz), 8.20 (1H, s), 8.86 (1H, m). MS (ES) m/z: 356.2 [M+H].

8L: 2-Benzimidazol-1-yl-N-(3'-methoxy-biphenyl-4-ylmethyl)-acetamide $^1$H NMR (400 MHz, DMSO-d$_6$) δ ppm 3.81 (3H, s), 4.38 (2H, d, J=8 Hz), 5.16 (2H, s), 6.95 (1H, d, J=8 Hz), 7.16 (1H, s), 7.22 (1H, d, J=8 Hz), 7.35-7.45 (5H, m), 7.61-7.68 (3H, m), 7.76 (1H, d, J=8 Hz), 8.82 (1H, s), 8.90 (1H, m). MS (ES) m/z: 372.0 [M+H].

8M: 2-Benzimidazol-1-yl-N-(2'-trifluoromethyl-biphenyl4-ylmethyl)-acetamide $^1$H NMR (400 MHz, DMSO-d$_6$) δ ppm 4.40 (2H, d, J=8 Hz), 5.15 (2H, s), 7.28-7.30 (2H, m), 7.32-7.40 (5H, m), 7.60-7.65 (2H, m), 7.70-7.77 (2H, m), 7.85 (1H, d, J=8 Hz), 8.69 (1H, s), 8.96 (1H, m). MS (ES) m/z: 4.10.4 [M+H].

8N: 2-Benzimidazol-1-yl-N-(3'-trifluoromethyl-biphenyl-4-ylmethyl)-acetamide $^1$H NMR (400 MHz, DMSO-d$_6$) δ ppm 4.40 (2H, d, J=8 Hz), 5.15 (2H, s), 7.32-7.42 (4H, m), 7.63 (1H, d, J=8 Hz), 7.70-7.78 (5H, m), 7.93-8.00 (2H, m), 8.65 (1H, s), 8.96 (1H, m). MS (ES) m/z: 409.8 [M+H].

8O: 2-Benzimidazol-1-yl-N-(2'-dimethylamino-biphenyl-4-ylmethyl)-acetamide $^1$H NMR (400 MHz, DMSO-d$_6$) δ ppm 2.70 (6H, s), 4.35 (2H, d, J=8 Hz), 5.12 (2H, s), 7.01 (1H, t, J=8 Hz), 7.08 (1H, d, J=8 Hz), 7.15 (1H, d, J=8 Hz), 7.25 (1H, t, J=8 Hz), 7.30-7.38 (4H, m), 7.50 (1H, d, J=8 Hz), 7.60 (1H, d, J=8 Hz), 7.73 (1H, d, J=8 Hz), 8.60 (1H, s), 8.88 (1H, m). MS (ES) m/z: 385.2 [M+H], 193.2, 180.2.

8P: 2-Benzimidazol-1-yl-N-(3'-methyl-biphenyl-3-ylmethyl)-acetamide $^1$H NMR (400 MHz, DMSO-d$_6$) δ ppm 2.38 (3H, s), 4.40 (2H, d, J=8 Hz), 5.12 (2H, s), 7.20 (1H, d, J=8 Hz), 7.26-7.48 (7H, m), 7.52-7.60 (3H, m), 7.72 (1H, d, J=8 Hz), 8.58 (1H, s), 8.90 (1H, m). MS (ES) m/z: 356.4 [M+H].

8Q: 2-Benzimidazol-1-yl-N-(3'-methoxy-biphenyl-3-ylmethyl)-acetamide $^1$H NMR (400 MHz, DMSO-d$_6$) δ ppm 3.82 (3H, s), 4.40 (2H, d, J=8 Hz), 5.12 (2H, s), 6.98 (1H, d, J=8 Hz), 7.18-7.20 (2H, m), 7.28-7.45 (5H, m), 7.55-7.58 (3H, m), 7.75 (1H, d, J=8 Hz), 8.68 (1H, s), 8.89 (1H, m). MS (ES) m/z: 372.2 [M+H].

8R: 2-Benzimidazol-1-yl-N-(2'-trifluoromethyl-biphenyl-3-ylmethyl)-acetamide $^1$H NMR (400 MHz, DMSO-d$_6$) δ ppm 4.40 (2H, d, J=8 Hz), 5.12 (2H, s), 7.18-7.41 (7H, m), 7.51 (1H, d, J=8 Hz), 7.62 (1H, t, J=8 Hz), 7.70-7.75 (2H, m), 7.84 (1H, d, J=8 Hz), 8.56 (1H, s), 8.90 (1H, m). MS (ES) m/z: 411.4 [M+H].

8S: 2-Benzimidazol-1-yl-N-(3'-trifluoromethyl-biphenyl-3-ylmethyl)-acetamide $^1$H NMR (400 MHz, DMSO-d$_6$) δ ppm 4.41 (2H, d, J=8 Hz), 5.12 (2H, s), 7.25-7.38 (3H, m), 7.45 (1H, t, J=8 Hz), 7.58-7.68 (3H, m), 7.70-7.78 (3H, m), 7.98 (2H, s), 8.65 (1H, s), 8.90 (1H, m). MS (ES) m/z: 411.4 [M+H].

EXAMPLE 9

Determination of In Vitro Activity

The functional activity of compounds at the TRPV1 receptor was determined using a Molecular Devices Flexstation II based $Ca^{2+}$ influx assay, employing a $Ca^{2+}$ sensitive fluorescent dye and a CHO cell line stably expressing human TRPV1 (VR1).

Test compounds were prepared as stock solution in DMSO and tested for activity over several log units (ranging 100 μM-100 pM). Compounds were further diluted in assay buffer as necessary for $IC_{50}$ determination.

CHO-K1 cells, stably expressing recombinant human VR1, under the control of a CMV promoter, were seeded (30,000 cells/well) in black clear-bottomed 96-well plates assay plates (Costar) 24 hr prior to assay. Cells were maintained at 37° C./5% $CO_2$ in normal growth medium (Dulbecco's Modified Eagles medium (DMEM/NUT.MIX.F-12 GLUTAMAX-1 (1:1) with PYRIDOXINE) supplemented with 10% fetalclone II serum and 0.4 mg/ml G418, all Invitrogen). Prior to assay, cells were washed once with assay buffer (150 μl, Hepes-buffered saline pH7.4, supplemented with 10 mM Glucose, 2 mM $CaCl_2$, 1 mM $MgCl_2$ and 0.5 mM Probenicid). Cells were then incubated in the dark with 100 μl 5 μM Fluo-3AM (Calbiochem) prepared in assay buffer for 1 hr at 37° C./5% $CO_2$. Excess dye was removed by washing the cells twice more with with buffer, prior to pre-incubation (10 min, RT) with an appropriate cocentration of test compound or buffer alone.

VR1 responses were assessed following addition, in the Flexstation II, of agonist (capsaicin) at an $EC_{80}$ concentration and $Ca^{2+}$ influx assessed by measurement of fluorescence emission (488 nm/525 nm). Baseline fluorescence responses were measured for approximately 20 s (16 reads at 1.28 s intervals) prior to addition of capsaicin. Increases in fluorescence emission following capsaicin addition were measured for a further 40 s (31 reads at 1.28 s intervals). Responses were recorded as Max-Min fluorescence. Antagonist induced inhibition of TRPV1 mediated increases in intracellular [$Ca^{2+}$] was assessed relative to wells on the same plate to which capsaicin was added in the absence of antagonist (i.e pre-incubation in buffer alone). Typical $IC_{50}$ values measured in the in vitro assay described above for the compounds of the invention are 3 μM or less. For several embodiments of the invention the $IC_{50}$ was found to be below 100 nM.

EXAMPLE 10

Formalin Test for Antinociception

The antinociceptive effects of test compounds were determined in the formalin paw test in mice. This model assesses behavioural responses to continuous, noxious stimulation generated by injured tissue. The injection of dilute solution of formalin into one hind paw of the mouse produces two distinct phases of nociceptive behaviour in several species (Dubuisson and Dennis, 1977). The first period begins immediately after formalin injection and lasts for 4-5 minutes. This early phase is followed by a period of 10-15 minutes of quiescent behaviour, after which a second phase of nociceptive behaviour occurs. This phase continues for a further 20-30 minutes. In mice, recording the time spent licking or biting the injected paw is the most common method of behavioural assessment.

Male ICR mice (22-30 g; n=6-10 per dose) were habituated to their test environment by placing them, singly, into clear Perspex observation boxes for 1 hour prior to drug administration on the day of the experiment. Formalin solution, 0.3% in sterile saline, was prepared as a fresh solution daily. Test compounds, dissolved in 5% solutol in water and were administered intravenously (i.v.), 10 ml·kg$^{-1}$, 5 minutes prior to the subcutaneous injection into the dorsal surface of one hind paw of 20 µl of formalin solution. The number of counts of nociceptive behaviour exhibited for each animal was then measured using an automated system. Nociceptive behaviour was measured during two time periods after formalin injection; 0-5 minutes (Phase 1) and 20-30 minutes (Phase 2). ED$_{50}$ values were calculated for each compound for each of the two phases of licking using a non-linear regression fit, sigmodal dose-response curve (Xlfit, IDDBs).

A typical ED$_{50}$ in phase II of the Formalin test is 50 µmol/Kg or less. For several compounds of the invention the ED$_{50}$ was found to be below 15 µmol/Kg.

The invention claimed is:

1. A 2-(benzimidazol-1-yl)-acetamide bisaryl compound of Formula I

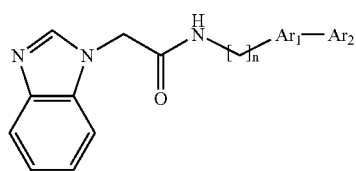

Formula I wherein n is 0 or 1;
Ar$_1$ represents a diradical derived from a 5- or 6-membered aromatic ring, optionally comprising 1-3 heteroatoms selected from N, O and S, said ring being optionally substituted with (C$_{1-4}$)alkyl, (C$_{1-4}$)alkyloxy, halogen, CF$_3$ or cyano;
Ar$_2$ represents a 6-membered aryl ring, optionally comprising 1-3 nitrogen atoms, said ring being optionally substituted with 1-3 substituents selected from (C$_{1-4}$)-alkyl (optionally substituted with 1 or more halogens), (C$_{1-4}$)alkyloxy (optionally substituted with 1 or more halogens), di(C$_{1-4}$)alkylamino, halogen, CF$_3$ or cyano; or a pharmaceutically acceptable salt thereof; with the proviso that compounds wherein n is 0 and —Ar$_1$— is a 2,4-thiazolylene or —Ar$_1$—Ar$_2$ represents 1,1'biphenyl)-2-yl are excluded.

2. The 2-(benzimidazol-1-yl)-acetamide bisaryl compound according to claim 1, wherein Ar$_1$ represents 1,3-phenylene, 2,6-pyridinylene, 1,3-pyrazolylene, 3,5-oxazolylene or 1,2,4-thiadiazol-3,5-diyl.

3. The 2-(benzimidazol-1-yl)-acetamide bisaryl compound according to claim 1, wherein Ar$_2$—Ar$_1$— represents 1-phenyl-1H-pyrazol-3-yl, 4-pyridin-2-yl-thiazol-2-yl or 3-phenyl-isoxazol-5-yl.

4. The 2-(benzimidazol-1-yl)-acetamide bisaryl compound according to claim 1, wherein n is 0 and Ar$_2$—Ar$_1$— represents 1-phenyl-1H-pyrazol-3-yl.

5. The 2-(benzimidazol-1-yl)-acetamide bisaryl compound according to claim 1 which is selected from the group consisting of:
2-benzimidazol-1-yl-N-biphenyl-3-yl-acetamide;
2-benzimidazol-1-yl-N-(2'-methoxy-biphenyl-3-yl)-acetamide;
2-benzimidazol-1-yl-N-(6-methoxy-biphenyl-3-yl)-acetamide;
2-benzimidazol-1-yl-N-(4-methyl-biphenyl-3-yl)-acetamide;
2-benzimidazol-1-yl-N-(4'-chloro-biphenyl-3-yl)-acetamide;
2-benzimidazol-1-yl-N-(4-methoxy-biphenyl-3-yl)-acetamide;
2-benzimidazol-1-yl-N-(2'-methyl-biphenyl-3-yl)-acetamide;
2-benzimidazol-1-yl-N-(6-phenyl-pyridin-2-yl)-acetamide;
2-benzimidazol-1-yl-N-biphenyl-3-ylmethyl-acetamide;
2-benzimidazol-1-yl-N-(3-phenyl-[1,2,4]thiadiazol-5-yl)-acetamide;
2-benzimidazol-1-yl-N-biphenyl-4-ylmethyl-acetamide;
2-benzimidazol-1-yl-N-biphenyl-2-ylmethyl-acetamide;
2-benzimidazol-1-yl-N-[1-(3-trifluoromethyl-phenyl)-1H-pyrazol-3-yl]-acetamide;
2-benzimidazol-1-yl-N-(1-phenyl-1H-pyrazol-3-yl)-acetamide;
2-benzimidazol-1-yl-N-[1-(4-trifluoromethyl-phenyl)-1H-pyrazol-3-yl]-acetamide;
2-benzimidazol-1-yl-N-[1-(3-methyl-phenyl)-1H-pyrazol-3-yl]-acetamide;
2-benzimidazol-1-yl-N-[1-(3-chloro-4-methyl-phenyl)-1H-pyrazol-3-yl]-acetamide;
2-benzimidazol-1-yl-N-[1-(3,5-difluoro-phenyl)-1H-pyrazol-3-yl]-acetamide;
2-benzimidazol-1-yl-N-[1-(3-fluoro-phenyl)-1H-pyrazol-3-yl]-acetamide;
2-benzimidazol-1-yl-N-[1-(3,4-difluoro-phenyl)-1H-pyrazol-3-yl]-acetamide;
2-benzimidazol-1-yl-N-[3-(6-methyl-pyridin-2-yl)-phenyl]-acetamide;
2-benzimidazol-1-yl-N-(3-m-tolyl-isoxazol-5-yl)-acetamide;
2-benzimidazol-1-yl-N-(2'-chloro-biphenyl-4-yl)-acetamide;
2-benzimidazol-1-yl-N-(3'-chloro-biphenyl-4-yl)-acetamide;
2-benzimidazol-1-yl-N-(3'-methoxy-biphenyl-4-yl)-acetamide;
2-benzimidazol-1-yl-N-(2'-methoxy-biphenyl-4-yl)-acetamide;
2-benzimidazol-1-yl-N-(4'-methyl-biphenyl-3-yl)-acetamide;
2-benzimidazol-1-yl-N-(4'-cyano-biphenyl-3-yl)-acetamide;
2-benzimidazol-1-yl-N-(3'-trifluoromethyl-biphenyl-3-yl)-acetamide;
2-benzimidazol-1-yl-N-(3'-cyano-biphenyl-3-yl)-acetamide;
2-benzimidazol-1-yl-N-(4'-methoxy-biphenyl-3-yl)-acetamide;
2-benzimidazol-1-yl-N-[3-(4-methyl-pyridin-2-yl)-phenyl]-acetamide;
2-benzimidazol-1-yl-N-[3-(4-trifluoromethyl-pyrimidin-2-yl)-phenyl]-acetamide;
2-benzimidazol-1-yl-N-(3'-methoxy-biphenyl-3-yl)-acetamide;

2-benzimidazol-1-yl-N-(3'-methyl-biphenyl-3-yl)-acetamide;
2-benzimidazol-1-yl-N-[3-(5-methyl-pyridin-2-yl)-phenyl]-acetamide;
2-benzimidazol-1-yl-N-[3-(5-trifluoromethyl-pyridin-2-yl)-phenyl]-acetamide;
2-benzimidazol-1-yl-N-[3-(6-trifluoromethyl-pyridin-2-yl)-phenyl]-acetamide;
2-benzimidazol-1-yl-N-(3'-trifluoromethoxy-biphenyl-3-yl)-acetamide;
2-benzimidazol-1-yl-N-[3-(4-trifluoromethyl-pyridin-2-yl)-phenyl]-acetamide;
2-benzimidazol-1-yl-N-(4'-methyl-biphenyl-2-ylmethyl)-acetamide;
2-benzimidazol-1-yl-N-(3'-methyl-biphenyl-2-ylmethyl)-acetamide;
2-benzimidazol-1-yl-N-(4'-chloro-biphenyl-2-ylmethyl)-acetamide;
2-benzimidazol-1-yl-N-(3'-chloro-biphenyl-2-ylmethyl)-acetamide;
2-benzimidazol-1-yl-N-(3',4'-difluoro-biphenyl-2-ylmethyl)-acetamide;
2-benzimidazol-1-yl-N-(4'-trifluoromethyl-biphenyl-2-ylmethyl)-acetamide;
2-benzimidazol-1-yl-N-(3'-trifluoromethyl-biphenyl-2-ylmethyl)-acetamide;
2-benzimidazol-1-yl-N-(3'-dimethylamino-biphenyl-2-ylmethyl)-acetamide;
2-benzimidazol-1-yl-N-(2'-methyl-biphenyl-4-ylmethyl)-acetamide;
2-benzimidazol-1-yl-N-(3'-methoxy-biphenyl-4-ylmethyl)-acetamide;
2-benzimidazol-1-yl-N-(2'-trifluoromethyl-biphenyl-4-ylmethyl)-acetamide;
2-benzimidazol-1-yl-N-(3'-trifluoromethyl-biphenyl-4-ylmethyl)-acetamide;
2-benzimidazol-1-yl-N-(2'-dimethylamino-biphenyl-4-ylmethyl)-acetamide;
2-benzimidazol-1-yl-N-(3'-methyl-biphenyl-3-ylmethyl)-acetamide;
2-benzimidazol-1-yl-N-(3'-methoxy-biphenyl-3-ylmethyl)-acetamide;
2-benzimidazol-1-yl-N-(2'-trifluoromethyl-biphenyl-3-ylmethyl)-acetamide; and
2-benzimidazol-1-yl-N-(3'-trifluoromethyl-biphenyl-3-ylmethyl)-acetamide;
or pharmaceutically acceptable salt thereof.

6. A pharmaceutical composition comprising a 2-(benzimidazol-1-yl)-acetamide bisaryl compound or a pharmaceutically acceptable salt thereof according to claim 1 in admixture with pharmaceutically acceptable auxiliaries.

7. The pharmaceutical composition according to claim 6, wherein in the 2-(benzimidazol-1-yl)-acetamide bisaryl compound of formula I, $Ar_1$ represents 1,3-phenylene, 2,6-pyridinylene, 1,3-pyrazolylene, 3,5-oxazolylene or 1,2,4-thiadiazol-3,5-diyl.

8. The pharmaceutical composition according to claim 6, wherein in the 2-(benzimidazol-1-yl)-acetamide bisaryl compound of formula I, $Ar_2$—$Ar_1$— represents 1-phenyl-1H-pyrazol-3-yl, 4-pyridin-2-yl-thiazol-2-yl or 3-phenyl-isoxazol-5-yl.

9. The pharmaceutical composition according to claim 6, wherein in the 2-(benzimidazol-1-yl)-acetamide bisaryl compound of formula I, n is 0 and $Ar_2$—$Ar_1$— represents 1-phenyl-1H-pyrazol-3-yl.

10. The pharmaceutical composition according to claim 6, wherein the 2-(benzimidazol-1-yl)-acetamide bisaryl compound is selected from the group consisting of:
2-benzimidazol-1-yl-N-biphenyl-3-yl-acetamide;
2-benzimidazol-1-yl-N-(2'-methoxy-biphenyl-3-yl)acetamide;
2-benzimidazol-1-yl-N-(6-methoxy-biphenyl-3yl)-acetamide;
2-benzimidazol-1-yl-N-(4-methyl-biphenyl-3-yl) acetamide;
2-benzimidazol-1-yl-N-(4'-chloro-biphenyl-3-yl)-acetamide;
2-benzimidazol-1-yl-N-(4methoxy-biphenyl-3-yl)-acetamide;
2-benzimidazol-1-yl-N-(2'-methyl-biphenyl-3-yl)acetamide;
2-benzimidazol-1-yl-N-(6-phenyl-pyridin-2-yl)-acetamide;
2-benzimidazol-1-yl-N--biphenyl-3-ylmethyl-acetamide;
2-benzimidazol-1-yl-N-(3-phenyl-[1,2,4]thiadiazol-5-yl)-acetamide;
2-benzimidazol-1-yl-N-biphenyl-4-ylmethyl-acetamide;
2-benzimidazol-1-yl-N-biphenyl-2-ylmethyl-acetamide;
2-benzimidazol-1-yl-N-[1-(3-trifluoromethyl-phenyl)-1H-pyrazol-3-yl]-acetamide;
2-benzimidazol-1-yl-N-(1-phenyl-1H-pyrazol-3-yl-acetamide;
2-benzimidazol-1-yl-N-[1-(4-trifluoromethyl-phenyl)-1H-pyrazol-3-yl]-acetamide;
2-benzimidazol-1-yl-N-[1-(3-methyl-phenyl)-1H-pyrazol-3-yl]-acetamide;
2-benzimidazol-1-yl-N-[1-(3-chloro-4-methyl-phenyl)-1H-pyrazol-3-yl]-acetamide;
2-benzimidazol-1-yl-N-[1-(3,5-difluoro-phenyl)-1H-pyrazol-3-yl]-acetamide;
2-benzimidazol-1-yl-N-[1-(3-fluoro-phenyl)-1H-pyrazol-3-yl]-acetamide;
2-benzimidazol-1-yl-N-[1-(3,4-difluoro-phenyl)-1H-pyrazol-3-yl]-acetamide;
2-benzimidazol-1-yl-N-[3-(6-methyl-pyridin-2-yl)-phenyl]-acetamide;
2-benzimidazol-1-yl-N-(3-m-tolyl-isoxazol-5-yl)-acetamide;
2-benzimidazol-1-yl-N-(2'-chloro-biphenyl-4-yl)-acetamide;
2-benzimidazol-1-yl-N-(3'-chloro-biphenyl-4-yl)-acetamide;
2-benzimidazol-1-yl-N-(3'-methoxy-biphenyl-4-yl)-acetamide;
2-benzimidazol-1-yl-N-(2'-methoxy-biphenyl-4-yl)-acetamide;
2-benzimidazol-1-yl-N-(4'-methyl-biphenyl-3-yl)-acetamide;
2-benzimidazol-1-N-(4'-cyano-biphenyl-3-yl)-acetamide:
2-benzimidazol-1-yl-N-(3'-trifluoromethyl-biphenyl-3-yl)-acetamide;
2-benzimidazol-1-yl-N-(3'-cyano-biphenyl-3-yl)-acetamide;
2-benzimidazol-1-yl-N-4'-methoxy-biphenyl-3-yl)-acetamide;
2-benzimidazol-1-yl-N-[3-(4-methyl-pyridin-2-yl)-phenyl]-acetamide;
2-benzimidazol-1-yl-N-[3-(4-trifluoromethyl-pyrimidin-2-yl)-phenyl]-acetamide;
2-benzimidazol-1-yl-N-(3'-methoxy-biphenyl-3-yl)-acetamide;

2-benzimidazol-1-yl-N-(3'-methyl-biphenyl-3-yl)-acetamide;
2-benzimidazol-1-yl-N-[3-(5-methyl-pyridin-2-yl)-phenyl]-acetamide;
2-benzimidazol-1-yl-N-[3-(5-trifluoromethyl-pyridin-2-yl)-phenyl]-acetamide;
2-benzimidazol-1-yl-N-[3-(6-trifluoromethyl-pyridin-2-yl)-phenyl]-acetamide;
2-benzimidazol-1-yl-N-(3'-trifluoromethoxy-biphenyl-3-yl)-acetamide;
2-benzimidazol-1-yl-N-[3-(4-trifluoromethyl-pyridin-2-yl)-phenyl]1-acetamide;
2-benzimidazol-1yl-N-(4'-methyl-biphenyl-2-ylmethyl)-acetamide;
2-benzimidazol-1yl-N-(3'-methyl-biphenyl-2-ylmethyl)-acetamide; 2-benzimidazol-1-yl-N-(4'-chloro-biphenyl-2-ylmethyl)-acetamide;
2-benzimidazol-1-yl-N-(340 -chloro-biphenyl-2-ylmethyl)-acetamide;
2-benzimidazol-1yl-N-(3',4'-difluoro-biphenyl-2-ylmethyl)-acetamide;
2-benzimidazol-1-yl-N-(4'-trifluoromethyl-biphenyl-2-ylmethyl)-acetamide;
2-benzimidazol-1-yl-N-(3'-trifluoromethyl-biphenyl-2-ylmethyl)-acetamide;
2-benzimidazol-1-yl-N-(3'-dimethylamino-biphenyl-2-ylmethyl)-acetamide;
2-benzimidazol-1-yl-N-(2'-methyl-biphenyl-4-ylmethyl)-acetamide;
2-benzimidazol-1-yl-N-(3'-methoxy-biphenyl-4-ylmethyl)-acetamide;
2-benzimidazol-1-yl-N-(2'-trifluoromethyl-biphenyl-4-ylmethyl)-acetamide;
2-benzimidazol-1-yl-N-(3'-trifluoromethyl-biphenyl-4-ylmethyl)-acetamide;
2-benzimidazol-1-yl-N-(2'-dimethylamino-biphenyl-4-ylmethyl)-acetamide;
2-benzimidazol-1-yl-N-(3'-methyl-biphenyl-3-ylmethyl)-acetamide;
2-benzimidazol-1-yl-N-(3'-methoxy-biphenyl-3-ylmethyl)-acetamide;
2-benzimidazol-1-yl-N-(2'-trifluoromethyl-biphenyl-3-ylmethyl)-acetamide; and
2-benzimidazol-1-yl-N-(3'-trifluoromethyl-biphenyl-3-ylmethyl)-acetamide;
or pharmaceutically acceptable salts thereof.

11. A method for treating a TRPV1 mediated disorder selected from the group consisting of acute and chronic neuropathic pain, and acute and chronic inflammatory pain in a subject in need thereof, comprising administering to the subject an effective amount of a 2-(benzimidazol-1-yl)-acetamide bisaryl compound or a pharmaceutically acceptable salt thereof according to claim 1.

12. The method for treating a TRPV1 mediated disorder according to claim 11, wherein the 2-(benzimidazol-1-yl)-acetamide bisaryl compound of formula I, $Ar_1$ represents 1,3-phenylene, 2,6-pyridinylene, 1,3-pyrazolylene, 3,5-oxazolylene or 1,2,4-thiadiazol-3,5-diyl.

13. The method for treating a TRPV1 mediated disorder according to claim 11, wherein the 2-(benzimidazol-1-yl)-acetamide bisaryl compound of formula I, $Ar_2$—$Ar_1$— represents 1-phenyl-1H-pyrazol-3-yl, 4-pyridin-2-yl-thiazol-2-yl or 3-phenyl-isoxazol-5-yl.

14. The method for treating a TRPV1 mediated disorder according to claim 11, wherein the 2-(benzimidazol-1-yl)-acetamide bisaryl compound of formula I, n is 0 and $Ar_2$—$Ar_1$— represents 1-phenyl-1H-pyrazol-3-yl.

15. The method for treating a TRPV1 mediated disorder according to claim 11, wherein the 2-(benzimidazol-1yl)-acetamide bisaryl compound is selected from the group consisting of:
2-benzimidazol-1-yl-N-biphenyl-3-yl-acetamide;
2-benzimidazol-1-yl-N-(2'-methoxy-biphenyl-3-yl)-acetamide;
2-benzimidazol-1-yl-N-(6-methoxy-biphenyl-3-yl)-acetamide;
2-benzimidazol-1-yl-N-(4-methyl-biphenyl-3-yl)-acetamide;
2-benzimidazol-1-yl-N-(4'-chloro-biphenyl-3-yl)-acetamide;
2-benzimidazol-1-yl-N-(4-methoxy-biphenyl-3-yl)-acetamide:
2-benzimidazol-1-yl-N-(2'-methyl-biphenyl-3-yl)-acetamide;
2-benzimidazol-1-yl-N-(6-phenyl-pyridin-2yl)-acetamide;
2-benzimidazol-1-yl-N-biphenyl-3-ylmethyl-acetamide;
2-benzimidazol-1-yl-N-(3-phenyl-[1,2,4]thiadiazol-5-yl)-acetamide;
2-benzimidazol-1-yl-N-biphenyl-4-ylmethyl-acetamide;
2-benzimidazol-1-yl-N-biphenyl-2-ylmethyl-acetamide;
2-benzimidazol-1-yl-N-[1-(3-trifluoromethyl-phenyl)-1H-pyrazol-3-yl]-acetamide;
2-benzimidazol-1-yl-N-(1-phenyl-1H-pyrazol-3-yl)-acetamide;
2-benzimidazol-1-yl-N-[1-(4-trifluoromethyl-phenyl)-1H-pyrazol-3-yl]-acetamide;
2-benzimidazol-1-yl-N-[1-(3-methyl-phenyl)-1H-pyrazol-3-yl]-acetamide;
2-benzimidazol-1-yl-N-[1-(3-chloro-4-methyl-phenyl)-1H-pyrazol-3-yl]-acetamide;
2-benzimidazol-1-yl-N-[1-(3,5-difluoro-phenyl)-1H-pyrazol-3-yl]-acetamide;
2-benzimidazol-1-yl-N-[1-(3-fluoro-phenyl)-1H-pyrazol-3-yl]-acetamide;
2-benzimidazol-1-yl-N-[1-(3,4-difluoro-phenyl)-1H-pyrazol-3-yl]-acetamide;
2-benzimidazol-1-yl-N-[3-(6-methyl-pyridin-2-yl)-phenyl]-acetamide;
2-benzimidazol-1-yl-N-(3-m-tolyl-isoxazol-5-yl)-acetamide;
2-benzimidazol-1-yl-N-(2'-chloro-biphenyl-4-yl)-acetamide;
2-benzimidazol-1-yl-N-(3'-chloro-biphenyl-4-yl)-acetamide;
2-benzimidazol-1-yl-N-(3'-methoxy-biphenyl-4-yl)-acetamide:
2-benzimidazol-1-yl-N-(2'-methoxy-biphenyl-4-yl)-acetamide;
2-benzimidazol-1-yl-N-(4'-methyl-biphenyl-3-yl)-acetamide;
2-benzimidazol-1-yl-N-(4'-cyano-biphenyl-3-yl)-acetamide;
2-benzimidazol-1-yl-N-(3'-trifluoromethyl-biphenyl-3-yl)-acetamide;
2-benzimidazol-1-yl-N-(3'-cyano-biphenyl-3-yl)-acetamide;
2-benzimidazol-1-yl-N-(4'-methoxy-biphenyl-3-yl)-acetamide;
2-benzimidazol-1-yl-N-[3-(4-methyl-pyridin-2-yl)-phenyl]-acetamide;
2-benzimidazol-1-yl-N-[3-(4-trifluoromethyl-pyrimidin-2-yl)-pheny]-acetamide;

2-benzimidazol-1-yl-N-(3'-methoxy-biphenyl-3-yl)-acetamide;
2-benzimidazol-1-yl-N-(3'-methyl-biphenyl-3-yl)-acetamide;
2-benzimidazol-1-yl-N-[3-(5-methyl-pyridin-2-yl)-phenyl]-acetamide;
2-benzimidazol-1-yl-N-[3-(5-trifluoromethyl-pyridin-2-yl)-phenyl]-acetamide;
2-benzimidazol-1-yl-N-[3-(6-trifluoromethyl-pyridin-2-yl)-phenyl]-acetamide;
2-benzimidazol-1-yl-N-(3'-trifluoromethoxy-biphenyl-3-yl)-acetamide;
2-benzimidazol-1-yl-N-[3-(4-trifluoromethyl-pyridin-2-yl)-phenyl]-acetamide;
2-benzimidazol-1-yl-N-(4'-methyl-biphenyl-2-ylmethyl)-acetamide;
2-benzimidazol-1-yl-N-(3'-methyl-biphenyl-2-ylmethyl)-acetamide;
2-benzimidazol-1-yl-N-(4'-chloro-biphenyl-2-ylmethyl)-acetamide;
2-benzimidazol-1-yl-N-(3'-chloro-biphenyl-2-ylmethyl)-acetamide;
2-benzimidazol-1-yl-N-(3',4'-difluoro-biphenyl-2-ylmethyl)-acetamide;
2-benzimidazol-1-yl-N-(4'-trifluoromethyl-biphenyl-2-ylmethyl)-acetamide;
2-benzimidazol-1-yl-N-(3'-trifluoromethyl-biphenyl-2-ylmethyl)-acetamide;
2-benzimidazol-1-yl-N-(3'-dimethylamino-biphenyl-2-ylmethyl)-acetamide;
2-benzimidazol-1-yl-N-(2'-methyl-biphenyl-4-ylmethyl)-acetamide:
2-benzimidazol-1-yl-N-(3'-methoxy-biphenyl-4-ylmethyl)-acetamide;
2-benzimidazol-1-yl-N-(2'-trifluoromethyl-biphenyl-4-ylmethyl)-acetamide;
2-benzimidazol-1-yl-N-(3'-trifluoromethyl-biphenyl-4-ylmethyl)-acetamide;
2-benzimidazol-1-yl-N-(2'-dimethylamino-biphenyl-4-ylmethyl)-acetamide;
2-benzimidazol-1-yl-N-(3'-methyl-biphenyl-3-ylmethyl)-acetamide;
2-benzimidazol-1-yl-N-(3'-methoxy-biphenyl-3-ylmethyl)-acetamide;
2-benzimidazol-1-yl-N-(2'-trifluoromethyl-biphenyl-3-ylmethyl)-acetamide; and
2-benzimidazol-1-yl-N-(3'-trifluoromethyl-biphenyl-3-ylmethyl)-acetamide;
or pharmaceutically acceptable salts thereof.

16. The method according to claim 11, wherein the subject is a human.

17. The method of claim 11, wherein the TRPV1 mediated disorder is acute and chronic neuropathic pain.

18. The method of claim 11, wherein the TRPV1 mediated disorder is acute and chronic inflammatory pain.

* * * * *